US005696981A

United States Patent [19]
Shovers

[11] Patent Number: 5,696,981
[45] Date of Patent: Dec. 9, 1997

[54] PERSONALITY ANALYZER

[76] Inventor: Aaron H. Shovers, 2704 Del Amo Blvd., Lakewood, Calif. 90712

[21] Appl. No.: 503,913

[22] Filed: Jul. 19, 1995

Related U.S. Application Data

[63] Continuation of Ser. No. 129,299, Sep. 30, 1993, abandoned.
[51] Int. Cl.$^6$ .............................. G06F 17/27; G06F 17/60
[52] U.S. Cl. ........................ 395/760; 395/759; 395/794; 395/201; 395/202; 434/236
[58] Field of Search ........................... 364/419.2, 419.08, 364/419.01, 401 R; 395/794, 759, 760, 201, 202; 434/236

[56] References Cited

U.S. PATENT DOCUMENTS

| | | | |
|---|---|---|---|
| 4,894,777 | 1/1990 | Negishi et al. | 364/419.2 |
| 4,908,758 | 3/1990 | Sanders | 364/419.2 |
| 4,930,077 | 5/1990 | Fan | 364/419.2 |
| 4,931,926 | 6/1990 | Tanaka et al. | 364/419.2 |
| 4,931,934 | 6/1990 | Snyder | 364/419.2 |
| 4,969,096 | 11/1990 | Rosen et al. | 364/413.02 |
| 5,219,322 | 6/1993 | Weathers | 600/27 |
| 5,243,517 | 9/1993 | Schmidt et al. | 364/419.2 |
| 5,251,131 | 10/1993 | Masand et al. | 364/419.08 |
| 5,371,673 | 12/1994 | Fan | 364/419.01 |
| 5,424,945 | 6/1995 | Bell | 364/419.2 |

OTHER PUBLICATIONS

1990–91, IPAT Catalog of Pyschological Assessment Instruments, Computer Interpretive Services, and Books.

Dr. Aaron H. Shovers, "Going to Excess", published by Three Dimensional Thinking, first copyrighted in 1988, pp. xi, 48–49, 89; 176–183, and 185–188.

Dialog File, 256, Acc. No. 01261343, Software Directory, Handwriting Analyst 3.2, first releasd Nov. 1986.

Dialog File 148, Acc. No. 05909600, Hopper et al, "A Script for Screening", *Security Management*, v. 36, No. 5, p. 72 (7 pages).

Dialog File 148, Acc. No. 0661505, Gladis "Are You the Write Type?", *Training & Development*, vol. 47, n. 7, p. 32 (4 pages).

*Primary Examiner*—Gail O. Hayes
*Assistant Examiner*—Joseph Thomas
*Attorney, Agent, or Firm*—Steven C. Sereboff; Riva W. Bickel

[57] ABSTRACT

Devices and methods for analyzing a subject's personality are provided using an automated personality analyzer. A subject's responses to a predefined quiz, responses to flashcards, a monograph, or a monologue, is used to determine the subject's likely personality type. The subject's choice and usage of words, and in particular certain "key words", are categorized, scored, and weighted in accordance with an aspect of the invention. The sums of these weighted scores are used to compare the subject to predefined pure personality type, so as to gain insight to the subject's psychological state and personality.

27 Claims, 12 Drawing Sheets

PERSONALITY ANALYZER

This is a continuation of application Ser. No. 08/129,299 filed on Sep. 30, 1993, now abandoned.

A portion of the disclosure of this patent document contains material which is subject to copyright protection. The copyright owner has no objection to the facsimile reproduction by any one of the patent disclosure, as it appears in the Patent and Trademark Office patent files or records, but otherwise reserves all copyright rights whatsoever.

BACKGROUND OF THE INVENTION

1. Field of the Invention

The present invention relates generally to systems and methods for analyzing the motivational philosophies of a person (what drives him to do whatever he is doing).

2. Description of Related Art

People have long had an interest in understanding our mental processes and behavior. Ancient civilizations, such as those of ancient India, Greece, and China, adopted formalized study of mental processes and behavior. For example, it is believed that in India, as long as three thousand years ago, serious attempts were made to study states of consciousness, dreams, and emotions. The early Greeks attempted to relate thoughts, moods and habits to changes in the physical state of the human body. One of the earliest debates amongst the Greek philosophers was whether human mental processes are inborn or whether they are a product of learning and experience.

Studies of psychology and behavior have continued to the present day. Yet, scientific attempts to classify and predict human mental processes and behavior have generally competed with spiritual and religious explanations. This crossover between science and religion flows naturally from the inseparability of philosophy and psychology.

The basis of much of modern philosophy and psychology arose in Germany, about 100 years ago. Psychologists such as Wundt, Fechner and Ebbinghaus are notable. However, it was not until the late nineteenth century that the science of psychology was introduced into America. Not coincidentally, it was a philosopher, William James, who was most notably active in this. Later, Edward Titchner, a member of the psychology department at Cornell University, argued strongly for the use of introspection as a technique for understanding mental processes.

At the beginning of the twentieth century, an American psychologist, John Watson, founded a movement known as behaviorism. According to the behaviorists, the study of mental processes was not properly the subject matter of psychology. They believed that science could be used to understand behavior, but only as a series of stimuli and responses. Watson himself claimed that consciousness or mental life is so subjective that scientific methods could not be used to study it. Despite the urgings of behaviorists to ignore mental processes, other schools developed. These include psychoanalysis and Gestalt psychology. According to Gestalt psychology, people can understand themselves (and be understood) only by looking at larger patterns of their experiences and actions. That is, Gestalt analysis holds that a person's mental processes are a result of many events that are acting upon a person over a given period of time, not just isolated stimuli.

It is well accepted that individuals trained in psychology have skill in understanding and predicting human nature. These individuals generally rely upon the known theories of human mental processes and behavior to arrive at conclusions regarding a given subject. Yet, the tools which such specialists typically use to analyze the personality of a subject have not changed appreciably in fifty years. Typical methods include conversing with the subject, and posing preconceived questions or a series of questions to the subject (including multiple-choice tests). While these methods are often adequate, they generally lack accuracy, reproducibility, and predictability. In other words, even today, psychology is not very scientific.

Also, the study of psychology itself has become complex, due to the fact that there are now hundreds of competing personality types, creating thousands of various motivational drives, which catalyze the millions of differing activities, among the billions of different hybrid personality types in the world. To understand the motivations behind a particular action done by a specific person, a psychologist would have to take all of the above factors into account (which is understood to be impossible).

Therefore, the inventor has utilized a different approach. The inventor accepts the fact that every "normal" person has a basic philosophy of life (and/or death), a way of relating his own self to other people and to the entire world about him. This basic philosophy or way of relating will be hereinafter referred to as a "personality type." It is one's personality type which provides a person with those basic beliefs that motivate him to do all the wonderful (or horrible) things he will be doing. Whereupon, success or failure in those activities will determine what his future personality type (or future philosophy) will be.

Basically, the Western world recognizes two philosophy types. The first philosophy type may be called the Realist, and the second the Idealist. Because these two belief systems may be identified with a person's behavior, they may also be considered to be personality types. A person of the Realist personality type is rational, pragmatic, materialistic, and active. A person of the Idealist personality type is a spiritual dreamer, concerned with abstract thoughts, and passive behavior. Because of the great dissimilarities in these two personality types, they result in two totally different languages—the preferred verbiage of the Realist and the words that best express the beliefs of the Idealist. A person of a given personality type (Realist or Idealist) will naturally utilize those words which best express his chosen personality type.

However, there is a big problem when we consider only these two personality types as the sole motivational forces behind all human action. For there are many motivations, beliefs, and goals which are not incorporated within these two personality types. Too many ideas and activities simply do not fall precisely into the pure Realist personality type or the pure Idealist personality type. Also, there are numerous overlapping concepts which both a Realist and an Idealist would accept as true.

Each person is believed to automatically select certain words (hereinafter called "key words") which best express the likes, dislikes, fears, and hates of that person, i.e the attitude of his personality type. Due to this, each type of person will develop his very own language. Each societal group also evolves its own ways of expressing its beliefs. Whereupon, each person consistently uses those same preferred key words most often and most emphatically during random speaking or writing.

It is therefore an object of the present invention to provide systems and methods for determining a subject's personality in an accurate, reproducible, scientific, and predictable manner. It is a further object to provide such a determination in an efficient and economical manner. These objects and others are provided in the personality analyzer of the present invention.

SUMMARY OF THE INVENTION

The invention is directed to devices and methods for analyzing a subject's personality type (leading to an analysis of his personality). In accordance with the invention, there is provided a computer system having a specialized program for analyzing a subject's personality type. Such a personality analyzer in accordance with the invention may base its analysis upon any of four sources of information respecting the subject: a questionnaire completed by the subject, a monograph written by the subject, flashcards, or a monologue by the subject. This information comprises the data input for the personality analyzer.

The invention is founded upon six personality types, which are believed to consider all possible time flames, all personality types, and all goals that humans can conceive. These six pure personality types are fully described in a book soon to be published, entitled Going to Excess, a draft of which is attached as Appendix C. By considering only six personality types, comprehending an individual's personality and behavior becomes both feasible and more precise than the methods presently used by psychologists.

The personality analyzer parses the data input for key words, and based upon the subject's usage of these key words, relates the subject's personality type to the pure personality types. Preferably, the key words are incorporated into the personality analyzer. Because categorizing the subject as either a Realist or Idealist is considered indefinite (with too many overlapping areas), the inventor has defined six personality types. These are the Novist, Revertist, Mutalist, Competist, Endurist and Centrist. The inventor has created six lists of key words which comprise the favorite verbiage for each of these personality types. These six lists are preferably utilized in the personality analyzer of the present invention. The way these words are expressed: favorably, neutrally, or unfavorably, can change the categorization of a found word. Also, repetitive use of a given word is preferably detected, with such repetitions being figured into the weightings. Since some words may be more significant to a particular personality type, words within the lists may have varying weight.

According to a preferred embodiment, when a key word is found in the input data, three context checks are performed to determine its category. In the first context check, the subject's emphasis of the found word is determined, so as to give it more value. Where the found word appears in only one key word list, the second context check is performed. In the second context check, whether the subject likes or dislikes the found word is determined, to determine which category this word should be in. If the found word appears in more than one key word list, the third context check is performed. In the third context check, it is determined which list the context of those found words indicate.

Within each of the context checks, the analyzer compares context words—a number of words immediately preceding and a number of words immediately following the found word—to lists of context-signaling words and their synonyms. By matching the context words to the context lists, the analyzer categorizes the context of the found word. Based upon these matches, the most likely meaning of the found word is determined and the found word is categorized based upon the key word lists.

More than just word usage is preferably considered. For example, where a questionnaire is the basis of data input, whether a question has been skipped by the subject is significant. Multiple usage of a single word is meaningful. Furthermore, long pauses in a monologue is also preferably considered.

Based upon the analysis of the key words, a correlation is made between the selected key words and the six pure personality types. This correlation may be expressed as a percentage, in a bar graph, a pie chart, or otherwise.

DESCRIPTION OF THE DRAWINGS

These and other advantages of the present invention are best understood with reference to the drawings, in which.

DETAILED DESCRIPTION OF THE PREFERRED EMBODIMENT

Figure 1:
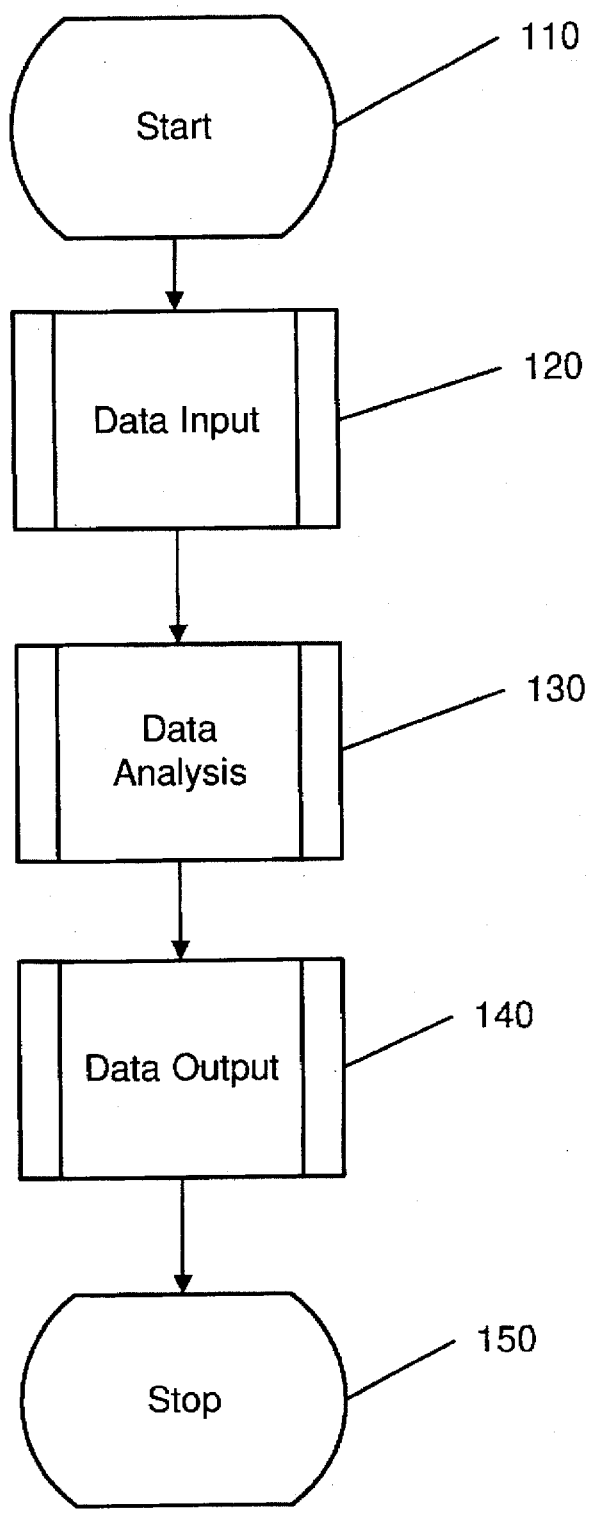
FIG. 1 is a general flow chart of the method of analyzing a subject's personality type in accordance with the present invention.

A personality analyzer and related methods according to an embodiment of the invention are described. Throughout this description, the preferred embodiment and examples shown should be considered as exemplars, rather than limitations on the method and apparatus of the present invention.

While a subject's personality may be partially understood through categorization of Realist or Idealist, it is preferred to use the categorization system unique to the inventor. It is considered that the Realist and Idealist types have considerable overlap and fail to account for all possible pure personality types. These two problems are substantially eliminated through the use of six types: Novism, Mutulism, Competism, Revertism, Endurism, and Centrism. The preferred categorization system is described in a book entitled, "Going to Excess," by Aaron Shovers and attached as Appendix C. Like the conventional system of categorization, each personality type of the preferred six-type system has a separate language. The particular key words of these languages have been placed by the inventor into lists. A first set of five lists are attached as Appendix A. In a second set of lists attached as Appendix B, there are provided three non-overlapping lists. In these three dual-use lists, Mutulism precisely opposes Competism, Novism precisely opposes Revertism, and Endurism precisely opposes Centrism.

Because it has been observed that certain key words are more important to a subject having a given personality than other key words which the subject may use, each key word in a list is preferably assigned a weighting. Also, when a key word fits more precisely into one particular belief system, that key word is preferably assigned a greater weight. In the lists in Appendices A and B, some words are capitalized or bolded, whereas other words are underlined. These differences indicate different weightings associated with such words. In particular, a greater weight is given to the most important and the most pure words for a given pure personality type. Those words which are bolded or capitalized are the most important and pure words, so they receive the greatest weighting. Those words which are underlined are of lesser import, so they are weighted a somewhat less. Those words which are neither capitalized, bolded, nor underlined have only a base weighting.

It has been found that the context of the words, as used by a subject, provides additional information relating to the subject's personality type. For example, the word "cooperate" is a word that a Mutulist may be inclined to use. However, if the same word is used by a subject in a disparaging manner, such use indicates the Competist personality type. Thus, contextual usage of a subject's words provide further important information. Therefore, in accordance with the invention, the preferred personality analyzer may check the context of each word selected by subject at three separate levels.

Within each of the context checks, the analyzer compares context words—a number of words immediately preceding and a number of words immediately following the found word—to lists of context-signaling words and their synonyms. By matching the context words to the context lists, the analyzer categorizes the context of the found word. Based upon these matches, the most likely meaning of the found word is determined and the found word is categorized based upon the key word lists.

At each context check, the five words immediately preceding the found word being analyzed and the five words immediately following the found word are isolated and compared to the words in the context lists. Based upon the correlation between these context words and the context lists, the context of the found word becomes known within a reasonable probability and the found word can be properly classified. If the context words do not provide sufficient correlation to a context list, a prototype meaning for that found word is accepted. The context checks are further described below.

The method for automatically analyzing a person's philosophy (to discover his personality) is now described. The personality analyzer is preferably realized as a general purpose computer system and a computer program for analyzing personality types. However, specialized devices are within the scope of the invention.

Referring now to FIG. 1, there is shown a flow chart for the personality analyzer in accordance with the present invention. After the program has been started (Step 110), a data input routine (Step 120) is performed. After the data has been inputted, the data is then analyzed in a data analysis step (Step 130). Finally, the analysis is output in a data output step (Step 140), and the program stops (Step 150). Alternatively, the process may be recursive, such that input is made only one or several words at a time, and after analysis of the input is complete, additional data is inputted.

There are two preferred embodiments of the personality analyzer of the present invention. According to the first preferred embodiment, the subject is given a questionnaire (or flashcards may be used), either in writing or orally. In the second preferred embodiment, the personality analyzer performs the analysis of a monologue or monograph of the subject. Because of the similarity of these two embodiments, and the considerable overlap of the data analysis portions, these two embodiments are described together.

Figures 2A, 2B:
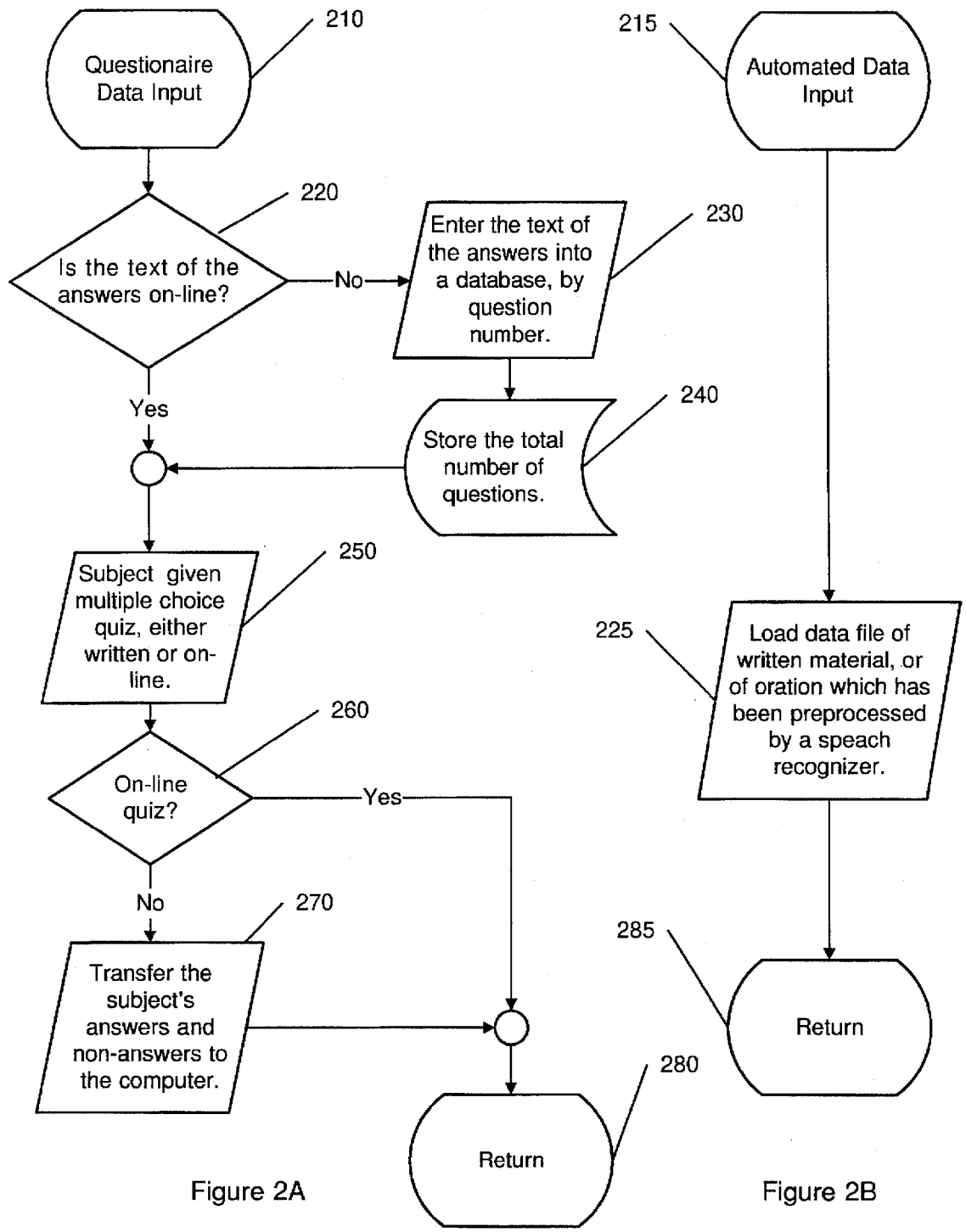
FIG. 2A is a flow chart of the data input routine shown in FIG. 1.
FIG. 2B is a flow chart of an alternative embodiment of the data input routine shown in FIG. 1.

As explained above, in Step 120, data is input into the personality analyzer. Referring now to FIG. 2A, where the data is input from a questionnaire or flashcards (Step 210), the analyzer first determines whether the text of the answers has already been stored (Step 220). If the text of the answers is not on line, the text of the answers must be made available to the analyzer. Preferably the answers are entered into a data base, organized by question number (Step 230). Next, the analyzer stores the total number of questions in the questionnaire (Step 240). The subject's answer to the multiple choice quiz are received (Step 250). This quiz may either be in writing, or it may be taken by the subject interactively with the personality analyzer. If the quiz is interactive, the analyzer presents the questions and the subject selects or enters an answer. By performing the quiz interactively, other information may be collected, such as time required to answer. Furthermore, the questionnaire may be changed during the subject's test, based upon the subject's answers. By basing the next question upon the subject's prior responses, the analyzer may focus on the subject's likely personality-type more efficiently and with higher accuracy. If the quiz is not on line, the subject's answers and non-answers must be transferred into the analyzer (Step 270). With the subject's answers and non-answers stored on line, data input from the questionnaire is now complete (Step 280).

Referring now to FIG. 2B, where data input is from a monologue or monograph by the subject (Step 215), data input is achieved simply by loading a data file of the monograph, or a digitized copy of the monologue into the computer (Step 225).

By monograph, it is meant a textual matter written or dictated by the subject, and may comprise, for example, letters, essays, books, and articles. By monologue, it is meant spoken matter by the subject, and may comprise a speech, the subject's part of a conversation, or even the responses to an interview. Preferably, the text is the product of a single person, alone, such that the words have been selected by that person. In contrast, a conversation comprises words selected by more than one person. Where a conversation is to be analyzed, additional tikering is necessary to separate the words of each conversant. Hence, the words of each conversant may be analyzed.

With either a monograph or monologue, the data is preferably fed into the computer using scanners, digitizers, etc. as is known in the art. If the data file is a monologue, the monologue may be simply preprocessed by a speech recognizer to produce a text file. Accordingly, the subject may speak into a microphone coupled to the analyzer. With the monograph or monologue stored in the analyzer, data input is complete (Step 285).

Referring again to FIG. 1, after there has been at least some data input (Step 120), the method then proceeds to data analysis (Step 130). Although the flow chart indicates serial flow of data input to data analysis, these two steps may also be embodied as data sources and data sinks, with data flowing between them as feedback or for concurrent processing.

Figures 3A, 3B:
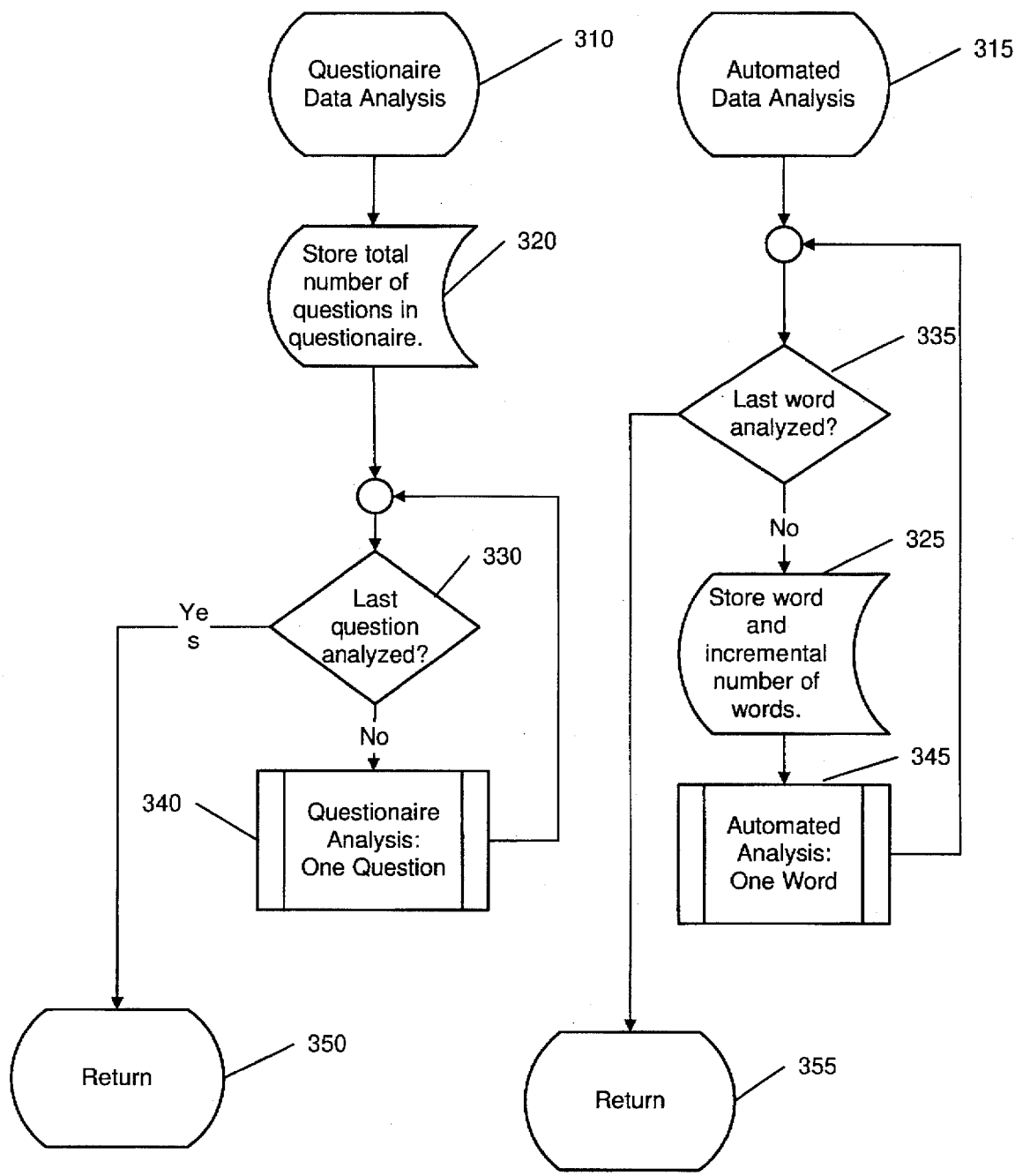
FIG. 3A is a flow chart of the data analysis routine shown in FIG. 1.
FIG. 3B is a flow chart of an alternative embodiment of the data analysis routine shown in FIG. 1.

Referring now to FIG. 3A, there is shown a flow diagram for data analysis (Step 130) where the data has been input from a questionnaire or flashcards (Step 310). The processing technique will be recognized as circular in nature, including a loop. As an initial step, the analyzer stores the total number of questions in the questionnaire (Step 320). Then the loop processing begins. At the top of the loop, it is determined whether the last question has been analyzed (Step 330). If the last question has not yet been analyzed, analysis then continues to a One Question Analysis routine (Step 340). On the other hand, if the last question has been analyzed, then processing ends (Step 350) so that output may be performed.

Referring now to FIG. 3B, there is shown the processing loop for data analysis when input is automated (Step 315). As with questionnaire data analysis, an initial step is to determine whether the end of the loop has been reached. In this regard, it is determined whether the last word in the data set has been analyzed (Step 335). If the last word has not yet been analyzed, the word under consideration is preferably stored, and a counter of the total number of words is incremented to reflect this word under analysis (Step 325). Subsequently, the word is analyzed in an Automated Analysis: One Word subroutine (Step 345). After the last word has been analyzed, processing returns (Step 355) back to the data output routine.

Figure 4A:
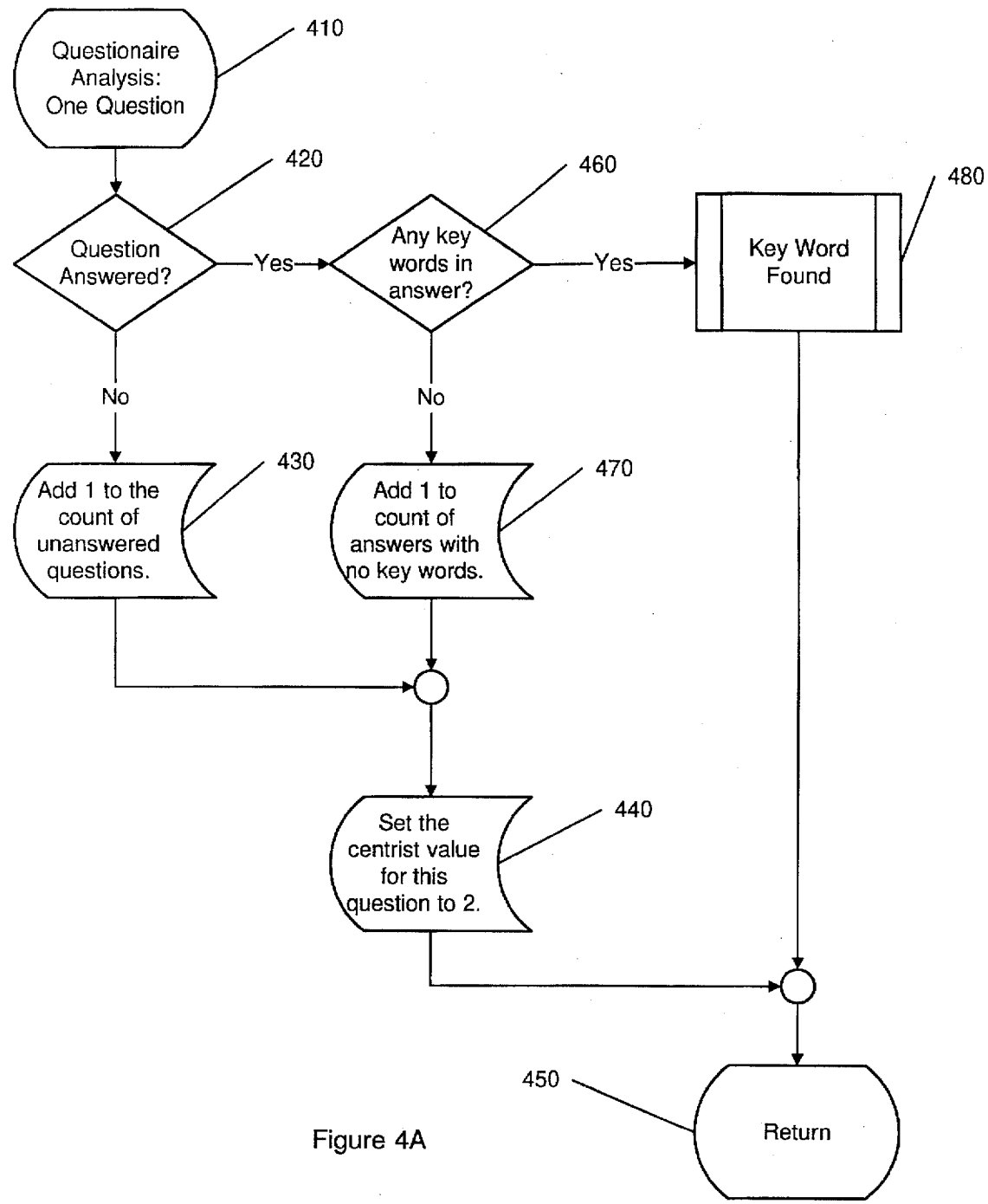
FIG. 4A is a flow chart of the Questionnaire Analysis: One Question routine shown in FIG. 3A.

Referring now to FIG. 4A, there is shown a further breakdown of the questionnaire data analysis routine, in particular, the Questionnaire Analysis: one Question subroutine (Step 410). In analyzing the answers to questions, it is first determined whether or not the subject has answered the question (Step 420). If the question has not been answered, then a count of unanswered questions is incremented (Step 430), the centrist value for this question is set to a value, preferably 2 (Step 440) and processing returns to the calling subroutine (Step 450). If the subject enters answers directly into the system, then the system preferably also measures and stores the time elapsed before an answer was made. This information provides additional insight into the subject's mental processes.

If the subject has answered the question (Step 420), then it is determined whether there are any key words in the answer (Step 460). If the subject has selected an answer with no key words, a count of the number of answers with no key words is incremented (Step 470), and the centrist value for this question is set to a value, preferably 2 (Step 440). After this setting step, processing returns (Step 450).

In the case where there are key words in the answer (Step 460), then further processing is done in a Key Word Found routine (Step 480), and processing returns (Step 450).

Figure 5:
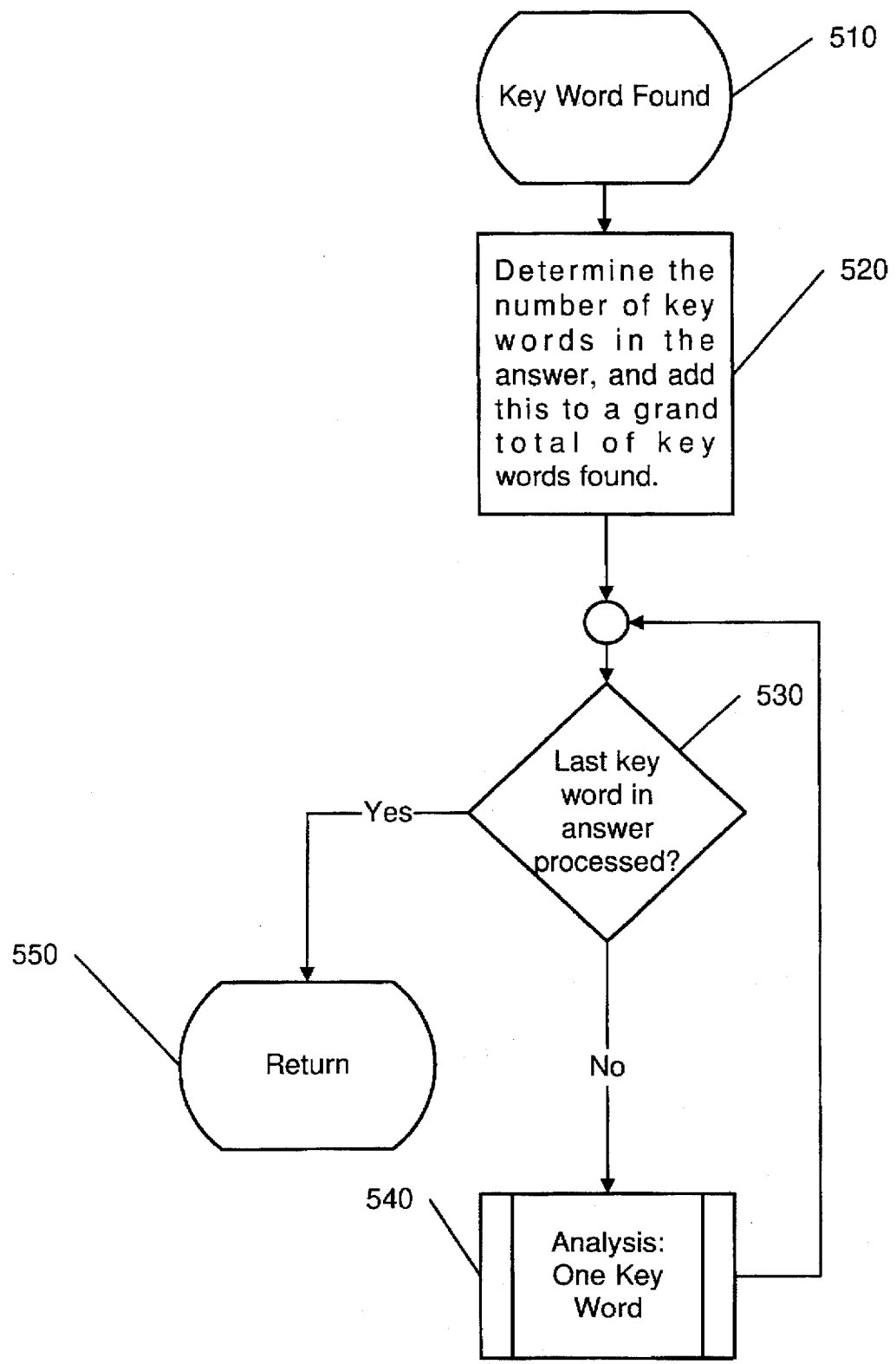
FIG. 5 is a flow chart of the Key Word Found routine shown in FIG. 4A.

Referring now to FIG. 5, there is shown the processing that takes place when a key word is found (Step 480). In this case (Step 510), the number of key words in the answer is counted, and this count is added to a grand total of key words found (Step 520). Next, another processing loop is performed. Firstly, it is determined whether the last key word in the answer has been processed (Step 530). If not, then analysis is made of the next key word in the answer, starting from the first key word which is in the answer (Step 540). After the last key word has been processed, processing returns (Step 550).

Figure 4B:
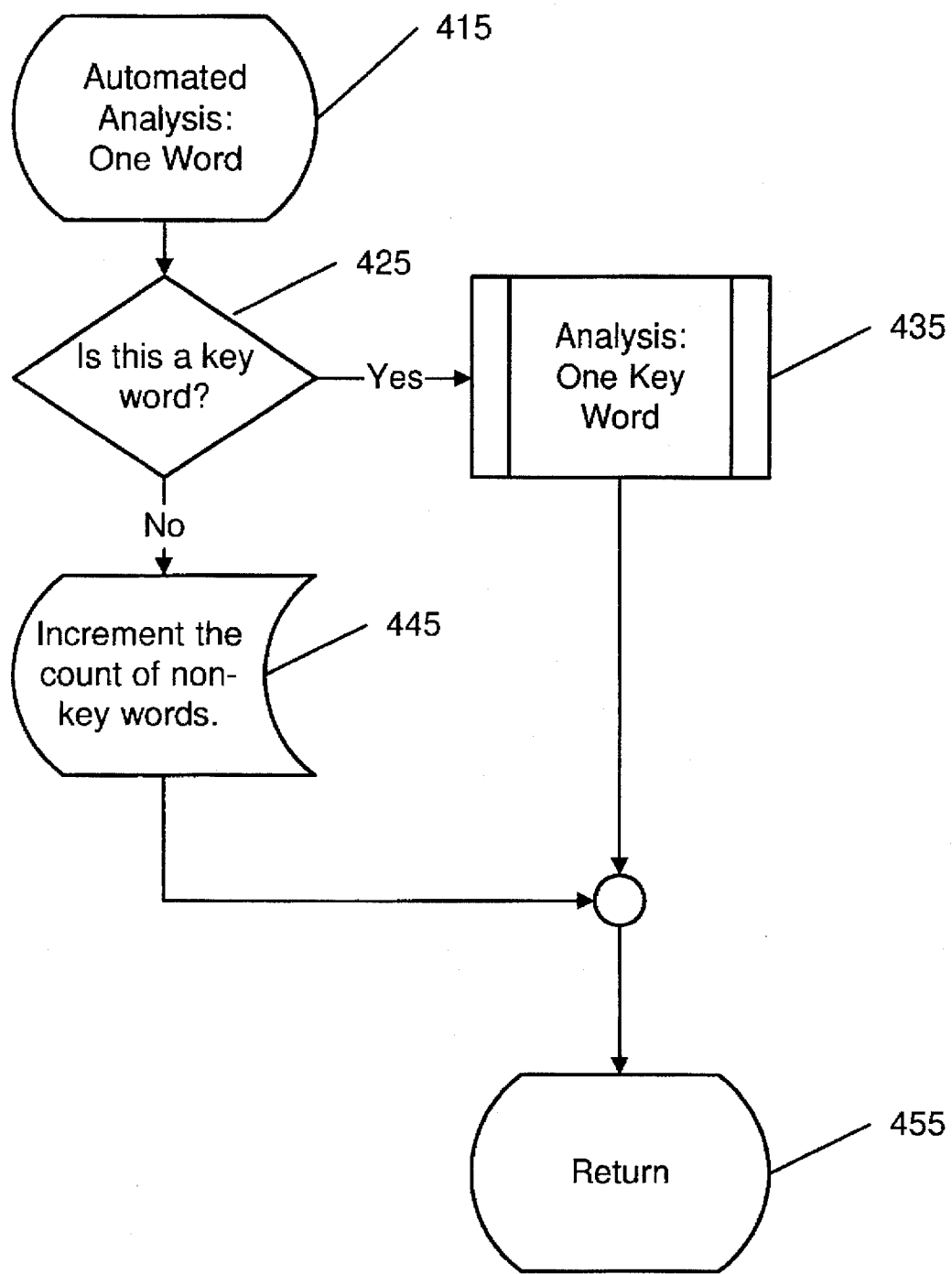
FIG. 4B is a flow chart of the Automated Analysis: One Word routine shown in FIG. 3B.

Referring now to FIG. 4B, there is shown the subroutine for processing one word when data input is automated. After the subroutine is entered (step 415), it is determined whether the found word is a key word (step 425). If the word is a key word, then the Analysis: One Key Word is performed (step 435). Otherwise, preferably a count of the number of non-key words is incremented (step 445). After either of these, processing returns (455).

Figure 6:
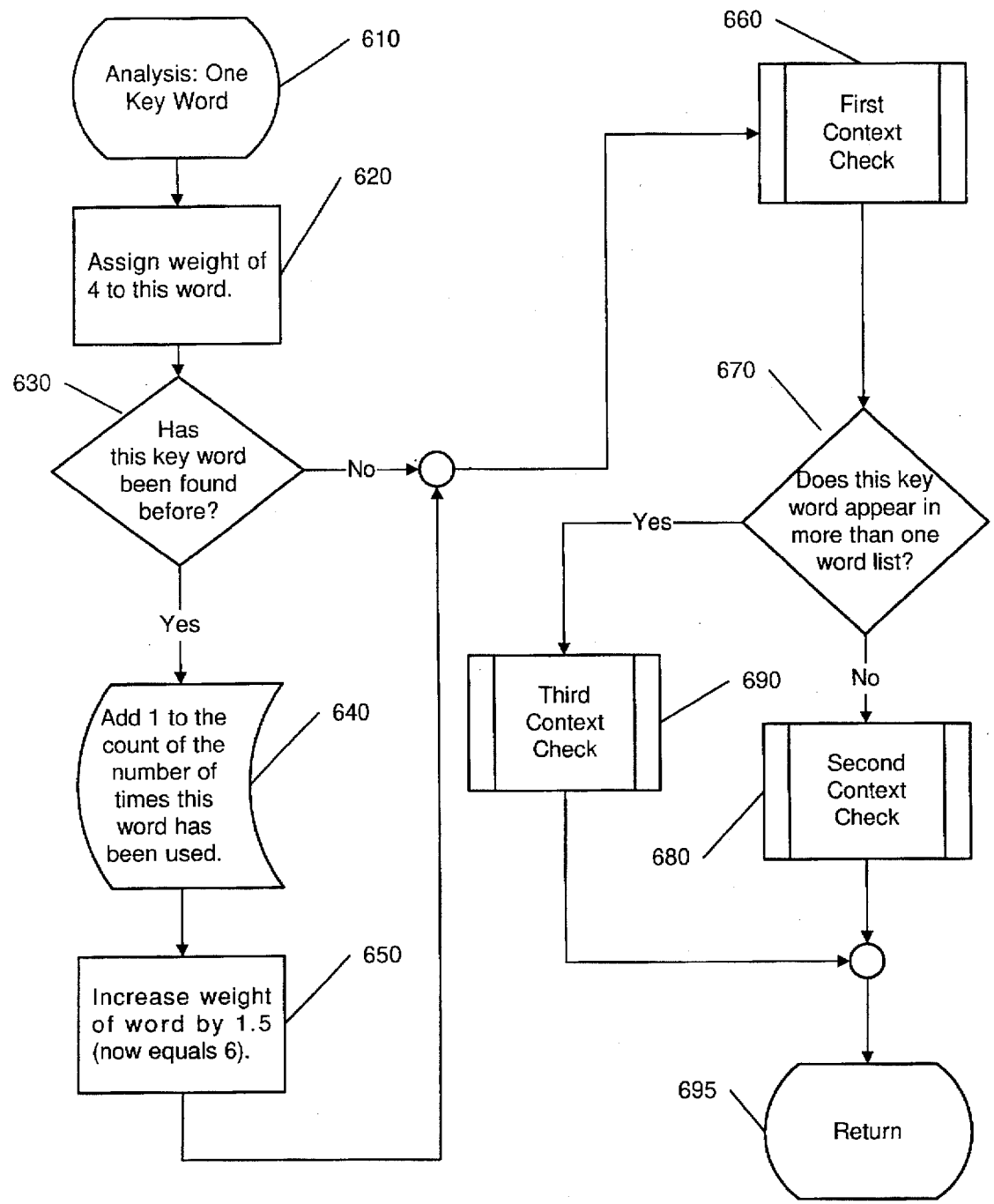
FIG. 6 is a flow chart of the Analysis: One Key Word routine shown in FIGS. 4B and 5.

Referring now to FIG. 6, there is shown the subroutine for processing a single key word. The One Key Word Found routine (Step 610) begins by initially assigning a weight of four m the particular word currently under analysis (Step 620). Next, it is determined whether the found word has been used or selected by the subject before (Step 630). If the found word has been found before, then additional weighting may be given to the word because of repeated use. In such case, a count of the number of times this particular word has been used is incremented (Step 640), and the weight of the word is increased by a weighting value, preferably 1½ times, to now equal six (Step 650).

Figure 7:
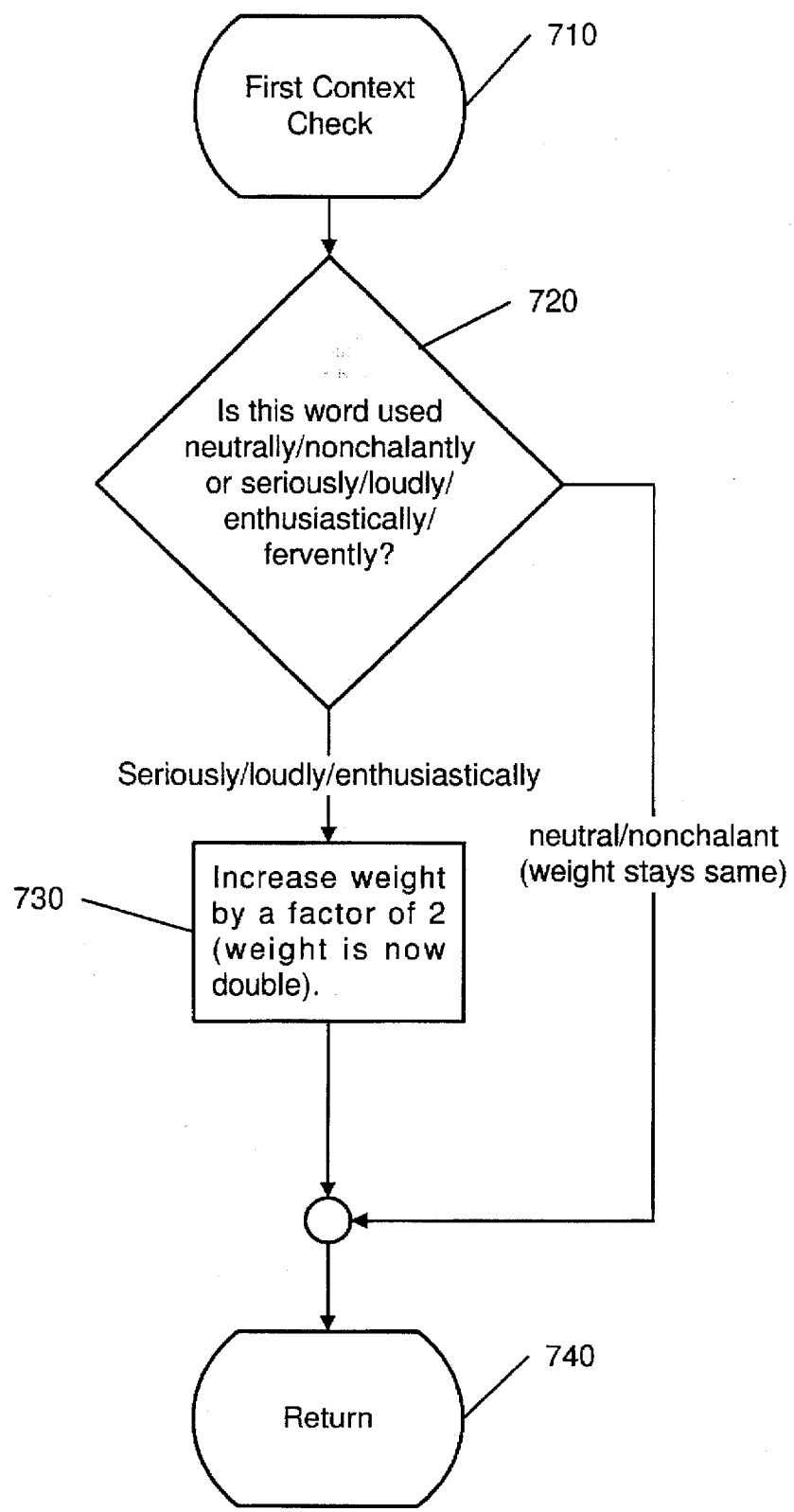
FIG. 7 is a flow chart of the First Context Check routine shown in FIG. 6.

After determining the current weight for the key word (either 4 points from Step 630 or 6 points from Step 650), a first context check is performed (Step 660 and 710 of FIG. 7). After completing the first context check, it is then determined whether this key word appears in more than one word list (Step 670). If the word appears in more than one word list, then a third context check is performed (Step 690 and 910 of FIG. 9); otherwise a second context check is performed (Step 680 and 810 of FIG. 8). Finally, processing returns to the calling process (Step 695). As exemplified by the lists in Appendix B, the list need not have any overlap. In such case, the test (Step 670) need not be performed, and processing continues to the second context check (Step 680).

Referring now to FIG. 7, there is shown the steps of the first context check (Step 710). In the first context check, it is determined whether the word has been used neutrally/ nonchalantly or seriously/loudly/enthusiastically/fervently (Step 720). If the subject's use of the word is neutral or nonchalant, then processing returns (Step 740, going to Step 670 in FIG. 6). On the other hand, if the word has been used seriously/loudly/enthusiastically/fervently, then the weight of the word is increased by a factor preferably of 2 (Step 730) prior to return (to Step 670 in FIG. 6).

Where the input is automated and obtained from an audio source, the system preferably also senses the relative volume of the words spoken. This is then factored into the first context check, or may replace it entirely. For example, if the volume increases on a key word, then the weight is increased; if the volume decreases or stays substantially constant, then the weight is unaffected.

Figure 8:
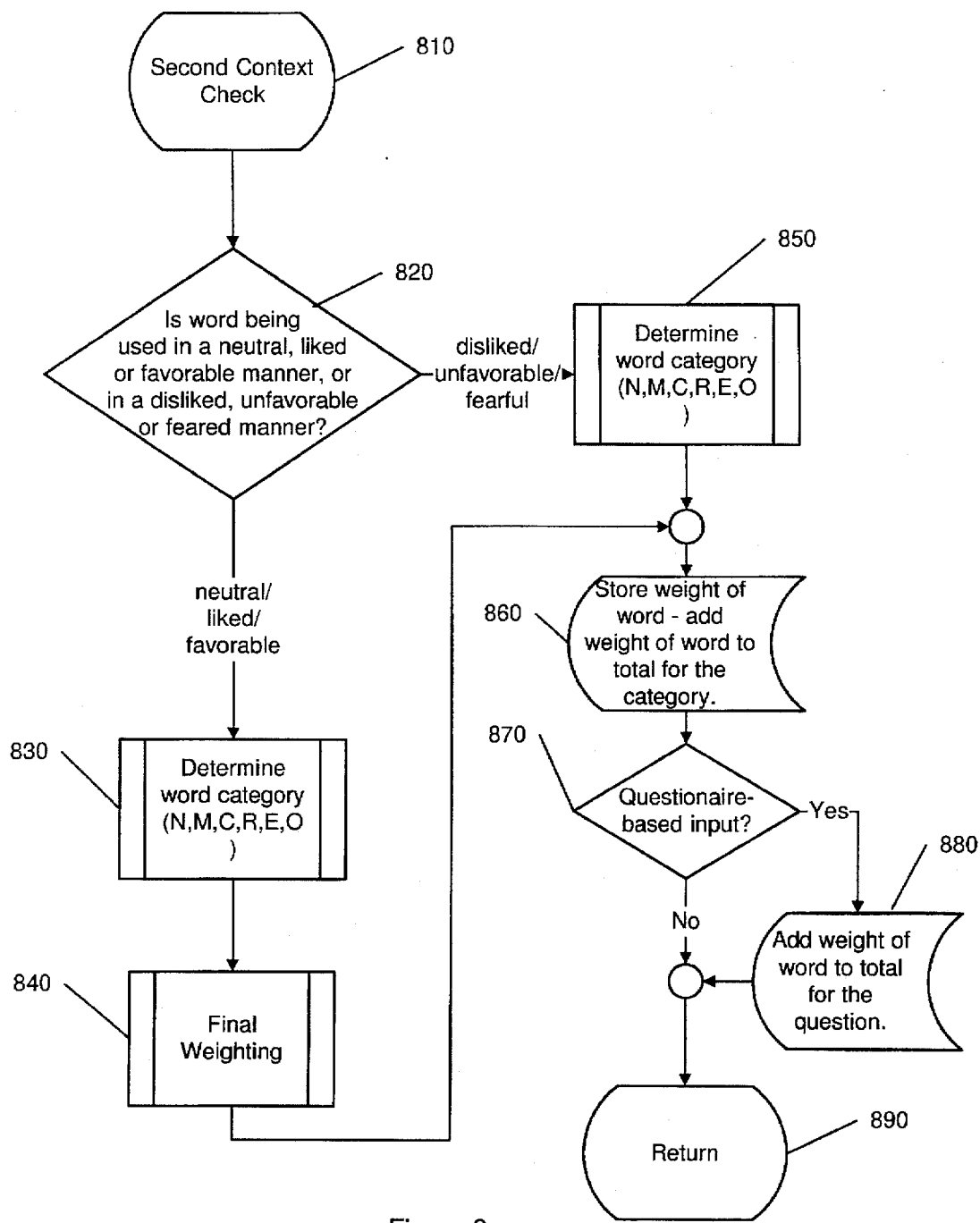
FIG. 8 is a flow chart of the Second Context Check routine shown in FIG. 6.

Referring now to FIG. 8, there is shown the steps for performing the second context check (Step 810). In performing the second context check, it is determined whether the word is being used in a neutral or favorable manner, or in a disliked, unfavorable or feared manner (Step 820). If the word has been used in a neutral, favorable or liked manner, it is then determined what category the word falls in (Step 830), and final weighting is performed (Step 840). On the other hand, if the word is used in an unfavorable or fearful manner, then it is directly determined which category the word falls in (Step 850). Next, the weight of the word is stored, and the weight is also added to the total for the appropriate category (Step 860). Next, if the analysis is questionnaire based (Step 870), then the weight of the word is also added to the total for the particular question (Step 880). Finally, processing returns to the calling process (Step 890).

Figure 9:
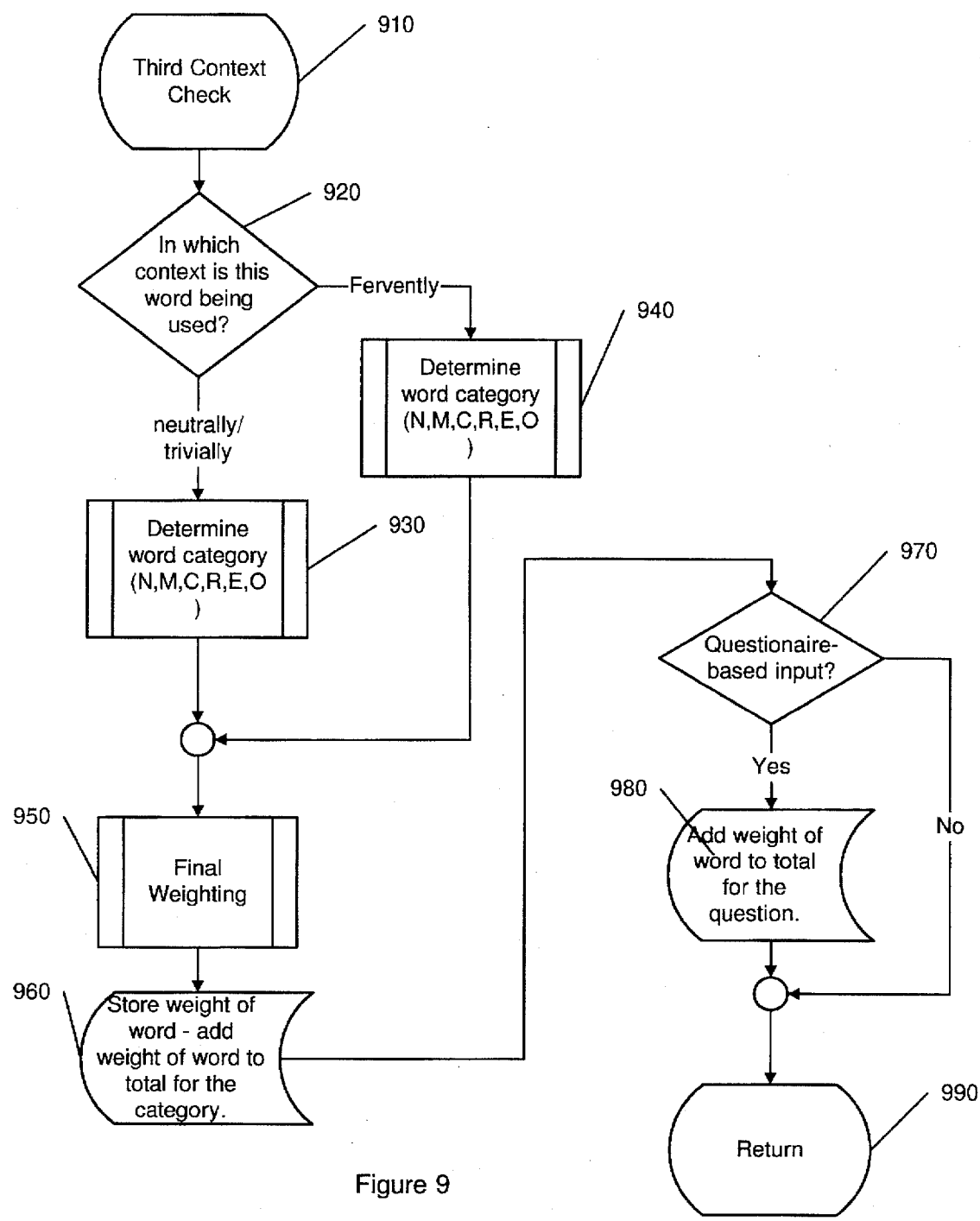
FIG. 9 is a flow chart of the Third Context Check routine shown in FIG. 6.

Referring now to FIG. 9, there are shown the steps of the third context check (Step 910). First, it is determined in which context the word is being used (Step 920). Accordingly, the word may be said to be used neutrally/trivially, or personally. By neutrally/trivially, it is meant to a moderate degree, oriented to the past or present times, involved physically or tangibly, or not personally involved. By personally, it is meant with great purpose or significance, important, oriented to the future, involved mentally or on an abstract level, or involving his or her own self. Based upon this determination, the particular category of the word may be determined (Step 930 or Step 940). After the context is checked, the final weighting is performed (Step 950) and the weight of the word is stored, and added to the total for the category (Step 960). If the analysis is questionnaire based (Step 970), then the weight of the word is also added to the total for the question (Step 980). Finally, processing returns to the calling process (Step 990).

Figure 10:
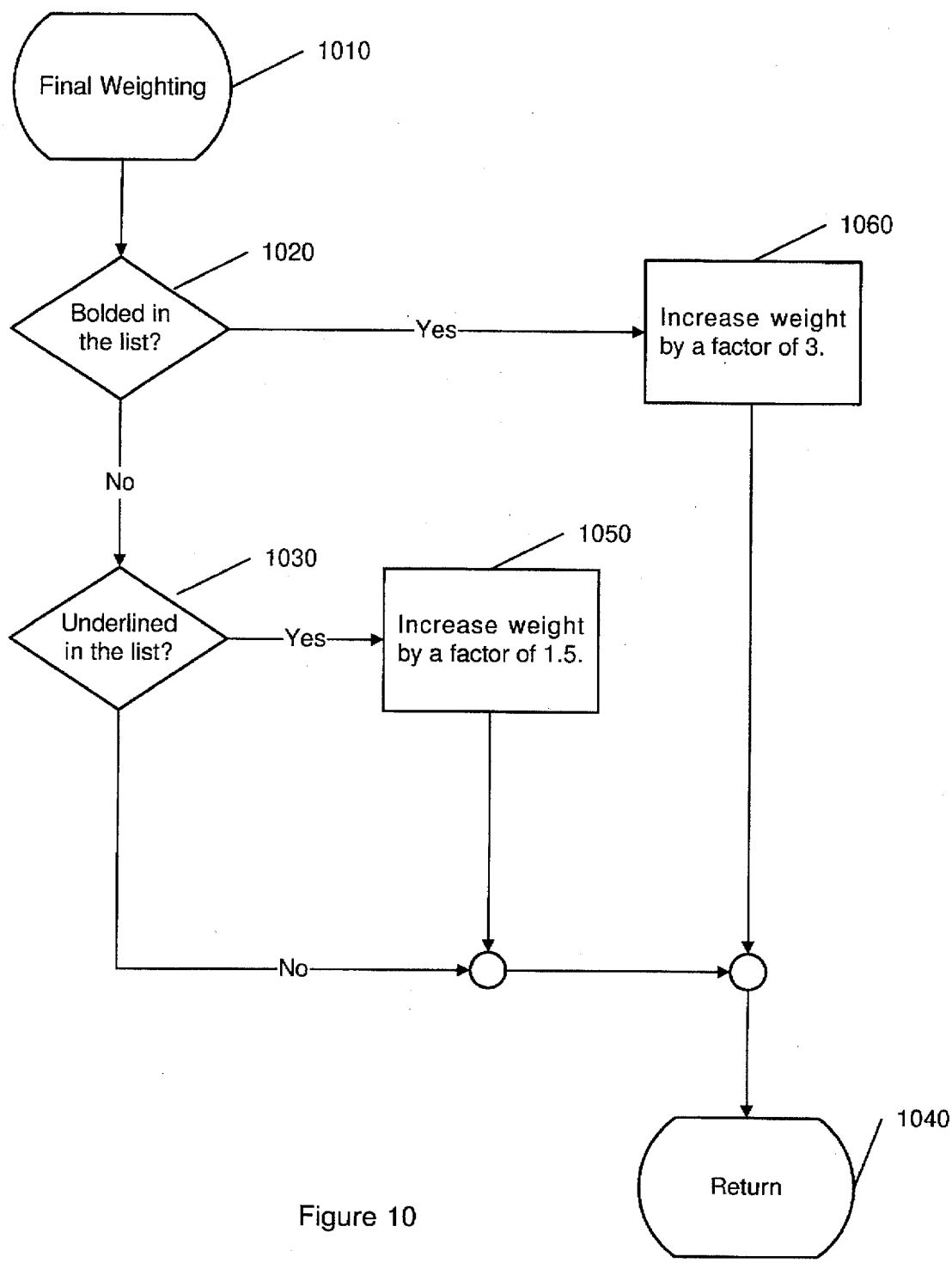
FIG. 10 is a flow chart of the Final Weighting routine shown in FIGS. 8 and 9.

Referring now to FIG. 10, there is shown the steps for the final weighting process (Step 1010). If the word is an important and most pure key word (capitalized or bolded in the appropriate list) (Step 1020), then the weight of the word is increased by a factor preferably of 3 (Step 1060). If the word is of lesser power (not capitalized or bolded, but underlined) (Step 1030), then the weight of the word is increased by a factor preferably of 1.5 (Step 1050). Finally, processing returns to the calling process (Step 1040). Those words which are neither capitalized, bolded, nor underlined retain only their present weights.

Figure 11:
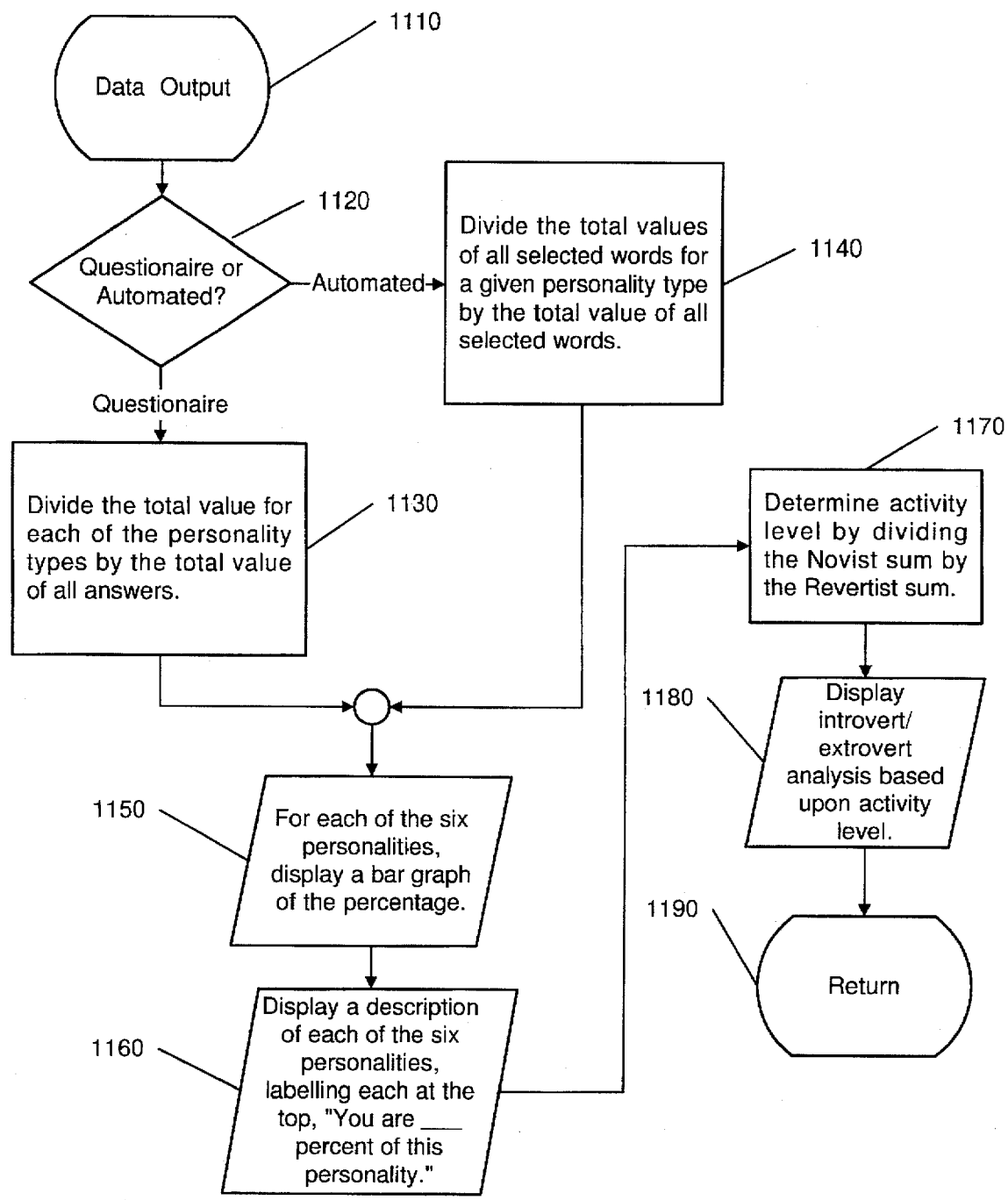
FIG. 11 is a flow chart of the data output routine shown in FIG. 1.

Referring now to FIG. 11, the steps for performing data output are shown (Step 1110). Output includes: the total count of all questions asked, the total count of all questions not answered, the total count of all answers which contained no key words, the total count of all the key words that were processed, and a list of all key words that were used more than once, and how often each one was utilized. As an option, the output can show how much time elapsed between the question being asked and the subject's answer. If the analysis has been questionnaire based or flashcard based (Step 1120), then a percentage for which the subject falls into each of the six personality types is determined by dividing the total value for all answers of each personality type by the total number of all questions asked (Step 1130). Similarly, if the analysis is automated, then a percentage for which the subject falls into each of the six personality types is calculated by dividing the total final value of all selected key words for a given personality type by the total number of all selected key words (Step 1140). In providing the data output, these percentages are preferably shown in bar graph form (Step 1150). Furthermore, a description of each of the six personality types is also preferably shown, labelling each personality as "You are _____ percent of this personality type." The activity level is also preferably shown, which comprises a ratio of the Novist sum to the Revertist sum (Step 1170). The activity level may be used to show the degree of introversion or extroversion of the subject person (Step 1180). After data output is complete, the process returns (Step 1190), and processing is complete.

Aspects of the present invention may be utilized to determine whether a text relates an honest expression by the subject. The inventor has found that a person who is lying typically has a delayed answering time. Furthermore, repeated use, or limited use, of particular key words also may indicate dishonesty. Hence, these qualities may be detected as explained, and an appropriate output may be made indicative of the honesty of the subject's expression.

For use as a diagnostic tool, these analyses provide indicia of stability or instability of the subject and the subject's state of mind. For example, where the input of a subject is especially indicative of a particular pure personality type, the subject is probably psychotic. The type of psychosis is the pure personality type. For example, where an analysis indicates that the subject is more than 85% limited into one personality type, that subject is probably psychotic in that regard.

Although exemplary embodiments of the present invention have been shown and described, it will be apparent to those having ordinary skill in the art that a number of changes, modifications, or alterations to the invention as described herein may be made, none of which depart from the spirit of the present invention. All such changes, modifications and alterations should therefore be seen as within the scope of the present invention.

Appendix A

Page 1 a. *"N" REFERS TO NOVISM. A 90% NOVIST LOVES THESE WORDS:*
OPTIMISM, positivism, hopes, hopeful, dreams, idealism, upbeat, cheerful
INTUITIVE, INSTINCTUAL, insight, subconscious, theoretical, visceral
INTELLECTUAL, INTELLIGENCE, wisdom, understanding, thinking, judgment, proficient, alert, adept, conscious, expert
EDUCATION, KNOWLEDGE, learn, learning, training, informed, enlightened, instruction, schooling, teaching, tutor,
ACTION, DOING, perform, accomplish, busy, dynamic, activate, react, deeds, exploits, energize, arouse, animated, vitality, vivacious, oomph
LIFE, LIFE-ORIENTED, alive, lively, buoyant, effervescent, vitality
SEX, procreate, propagate, reproduction, erotic, lust, spicy, risque, racy, suggestive, exotic
INVINCIBLE, UNLIMITED, POTENT, COURAGE, powerful, invulnerable, unbeatable, indomitable, brave, fearless, unafraid, valiant, confident, self-confident, over-confident, untouchable, daring, audacious, impetuous, cocky, cock sure
ADVENTURE, CHALLENGES, DANGER, exploration, adversity, peril, risk, hazards, exploits, quest, chances, explore, ventures
EXCITEMENT, PLAY, thrills, entertainment, stimulation, fascinating, intriguing, enthralling
CAREFREE, CARELESS, UNPREDICTABLE, IMPULSIVE, ANYWHERE, ANYTIME, reckless, unplanned, spontaneous, extemporaneous, uncertainty, unsureness, changeable, changing times, volatile, capricious, erratic, fickle, impromptu, variable, inconstant, unstable, temperamental, mercurial, happy-go-lucky, foolhardy, license, improvised, spur of the moment, offhand, politically on the radical side
CURIOUS, CURIOSITY, inquisitive, questioning, wonder, searching, interest, inquiring, examining, unusual, oddity, peculiar, bizarre, new, novel
DISCOVERY, reveal, revelation, disclose, expose, aware, ascertain, determine, find out, detect, discern, observe, perceive
INNOVATIVE, INVENTIVE, CREATIVE, ingenious, original
EXTROVERT, outwardly-oriented, overt
FREE-WILL, FREE, FREEDOM, self-determination, liberty, voluntarily, willfully, without coercion, rights, unrestrained, released, having choices, options, prerogatives, fancy-free, scot-free
NONCONFORMITY, UNDISCIPLINED, DISPROVE, REBELLING, ANARCHY, DISORDER, dissent, insurgent, mutiny, lawlessness, alienation, disintegration, estrangement, unorthodox b. *A 90% NOVIST HATES THESE WORDS (when referring to him or her, personally):*
FORCED, COMPELLED, coerced to do something
BOREDOM, MONOTONY, tedium, dull, familiar things, dreary, drudging, tiresome, tiring
INACTIVITY, THE STATUS QUO, static, inaction, idleness, quiet, sedentary, dormant, lethargy, sleep, asleep, sleepy
PESSIMISM, IMPOTENCE, weak, defeatism, despair, hopelessness, gloom, doubters, cynics, sceptics, worrywarts
CONFORMITY, OBEDIENCE, obey, harmonize, fit in, integrate, accomodation, comply
AUTHORITIES, CONTROL, rulers, rules, leaders, laws, edicts, regulations, statutes, bondage, slavery, serfdom, commands, mandates, controls, domination
INTROVERTED, withdrawn, inhibited, restrained
PLANNING, PLANNED, FIXED PRINCIPLES, ORDERLINESS, orderly, organized, well-organized, systematized, methodical, well thought out, with a game plan Page 2 a. *"M" REFERS TO MUTULISM. A 90% MUTULIST idealizes (referring to people):*

LOVE, LOVING, LOVABLE, AGREE, AGREEMENT, CONCUR, approval, accord, benevolent, humanitarian, compatible, congenial, rapport, charitable, altruism, agreeable, likable, genial, cordial, good-natured, favor, dote, devotion
WE, FRIENDS, FAMILY, friendly, children, sociable, coexist, unite, ally, companion, mate, gregarious, associates, relationships, tribe, community, society, fellowship, club, fraternity, sorority, concord, accompanied, home, other persons, people, the public
HUMANITY, HUMANS, mankind, Man (in the generic sense, including women), contemporaries
TRUST, TRUSTWORTHY, RELIABLE, HONEST, justice, dependable, responsible, duty, faithful, humane, righteous, upright, honorable, decent, good, high-principled, the needs of other people, reliance, dependence, entrust, ethics, manners
COOPERATION, COOPERATIVE, NONCOMPETITIVE, AGREEMENT, collaborating, harmonize, serve, synergism, concur, in concert, politically a "bleeding heart" LIBERAL
RESPECT, RESPECTABLE, PRAISE, COMPLIMENT, self-image, acceptance, status, esteem, commend, acclaim, admire, applause
EMOTIONAL, DEPENDENT UPON OTHERS, TALK, TALKATIVE, VOCAL, sensitive, responsive, responsiveness, warmth, romantic, softhearted, sympathetic, kindhearted, kind, considerate, compassionate, understanding, has feelings, outspoken, openness, impractical, unrealistic, dreams, dreamy, starry-eyed, poetry, art, artistic,
DISSATISFIED, DISCONTENTED, disgruntled, malcontent, ungratified, politically on the LEFT
FUTURE (an improved future), high expectations, afterwards b. *A 90% MUTULIST HATES THESE WORDS (referring to persons):*

COMPETITION, CONTROVERSY, FIGHT, QUARREL, contention, argument, dispute, conflict, dominate, control, superiority, supremacy
LONELINESS, LONELY, ALONE, LONESOME, egocentric, individualism, solitary, separated, abandoned, deserted, forsaken, isolated, remote
HATE, DESPISE, DETEST, LOATHE, resent, repulsive, malicious, viscious, horrible, horrid, mean, obnoxious, contemptible, despicable, reprehensible, repugnant, revulsion, resentful, nasty, spiteful, scorn, disdain, dislike, detest, evil, enmity, odious, aversion, antagonism, animosity, abhor, vile, hostility, bitchy, catty
BLAME, CRITICISM, condemn, ostracize, denounce, accuse, reproach, fault, knock, censure, impeach, exile, expulsion, banish, expel, throw out, deport, guilt feelings, delinquent
IRRESPONSIBLE, UNRELIABLE, UNTRUSTWORTHY, NOT DEPENDABLE, fickle, inconstant, unstable, careless, reckless, questionable, unsure, vacillating, shifty
BETRAYAL, DECEIVED, deluded, misleading, dishonest, double-crossed, disloyal, sold out, taken in, infidelity, beguiled, sold down the river, unfair, broke faith, unfaithful, faithless
TREACHERY, TRAITOROUS, TREASON, EVIL PEOPLE, underhanded, secretive, sly, sneaky, devious, tricky, informers, squealers, stool pigeon, talebearer, tattler, tattletale
FRUSTRATIONS, disappoint, preclude, block, hinder, impede, obstruct, upset Page 3 a. "C" STANDS FOR _COMPETISM_, A 90% COMPETIST PREFERS THESE WORDS:

INDEPENDENCE, INDEPENDENT, "I", INDIVIDUAL, INDIVIDUALSIM, self-reliance, self-sufficient, self-supported, privacy, personal, sovereign, autonomous, on one's own, egocentric, singular, solo, separate, single, selfish, confidentially, silence, secrets, secretive, concealment, hush-hush, clanestine, covert, subterfuge, subrosa, undercover, hidden, behind closed doors, on the Q.T., under the table, politically CONSERVATIVE MATERIALISM, TANGIBLES, REALISM, REALITY, REAL, SCIENTIFIC, CONCEPTS, FACTS, profit, things, house, food, car, appliances, devices, physical, entity, concrete, actual, actually, actuality, components, parts, factors, elements, ingredients, apparatus, equipment, machine, gear, outfits, clothing, objects, objective, matter-of-fact, palpable, perceptible, embody, paraphernalia, stuff, redundancy, superfluous, substance, substantially, animal, carnal, body, body image (skin, muscles, fat)

PRACTICAL, PRAGMATIC, functional, workable, useful, utilitarian, constuctive, applicable, feasible, implicit, LOGICAL, RATIONAL, RATIONALE, RATIONALIZE, ORGANIZE, ORGANIZED, SYSTEMS, SYSTEMATIC, SYSTEMATIZE, JUSTIFY, JUSTIFIED, WHY? calculating, analytical, plan, planning, deliberate, design, designing, deduce, derive, strategy, well-organized, methodical, methods, obvious, self-evident, pertinent, fundamental, basic, valid, applicable, straightforward, clear, proof, germane, manifest, discerning, cogitate, perceptive, plain, lucid IMPERSONAL, UNEMOTIONAL, detached, reserved, unfeeling, cold, cold-blooded SELF-ASSURANCE, CAPABLE, ABLE, ABILITY, COMPETENCE, QUALIFIED, effective, competent, adept, tested, trained, proven, fit WORK, JOB, OCCUPATION, CAREER, livelyhood, labor, business, employment, profession, trade, vocation, craft, chores, hard work, strive, toil, effort, make an effort, try, attempt, exertion, perform, handicraft, procedures, process, operate, use, function COMPETE, COMPETITION, WIN, GAIN, superiority, supremacy, overcome, prevail, triumph, victory, dominate, dominant, power, strong, strength, mighty, competitor, rival, enemy, opportunity, contend, contest, conflict, aggression, dispute, fight, battle, war, warfare, tug-of-war, struggle, exploit, influence OPPORTUNITY, OPPORTUNISTIC, well-timed, auspicious, an opening, a good break, a good chance for success, promising circumstances, the favorable time and the proper occasion SURVIVAL, outlive, outlast, continue, persist, exist, come through, pull through, carry on WEALTH, WEALTHY, RICH, PROSPERITY, FINANCIAL INDEPENDENCE, affluence, abundance, financial well-being, economic prosperity, riches, NOW, TODAY, IMMEDIATELY, RIGHT AWAY, DURING THIS LIFETIME, the present times, nowadays, at once, instantly HERE, IN THIS WORLD, WORLDLY, SECULAR, earthly, down-to-earth, in this place, in this vicinity, mundane, temporal Page 4 b. *A 90% COMPETIST DETESTS THESE WORDS:*

SPIRITUAL, UNREAL, ABSTRACT, INTANGIBLE, symbolic, occult, immaterial, unworldy, heavenly

POVERTY, FINANCIAL DEPENDENCE, poor, impoverished, dependent, relying on others, reliant, bankrupt, unemployed, indigence, destitution, going broke, economic collapse, hit the skids, terminated, welfare, privation

LOSING, GIVING UP, SURRENDER, RESIGN, forfeit, yield, relinquish,

LOSS OF CONTROL, INCAPACITY, DEATH, incapable, inability, inadequate, ineffective, ineffectual, weak, weakness, decrepit, feeble, frail, debilitated, inferior, impotent, powerless, unreliable, unfit, unqualified, not effective, deceased, demise, grim reaper, grave, fatal, lethal, corpse, cadaver, ghost

FAILURE, MISTAKES, ERROR, blunder, miscalculate, misjudge, confusion, mixed up, misconstrue, blooper, slipup, make a boo-boo, bungle, louse up, screw up, misinterpret

EMOTIONS, EMOTIONAL, FEELINGS, sentimental, sensitive, softhearted, affection, passion

OTHER PEOPLE'S NEEDS, communicating with other people

*"R" STANDS FOR REVERTISM, A 90% REVERTIST PREFERS THESE WORDS:*
SAFE, SAFEGUARD, SECURE, SECURITY, PROTECTION, PRESERVATION, PREVENTION,
  AVOIDING COSTLY OR STUPID ACTIONS, CAREFUL, CAUTIOUS, wary, riskless, guard,
  defend, defense, safeguard, shelter, shield, limits, inhibit, subdued, repressed, restrain,
  restrained, circumspect, discreet, unhurt
PAST TMES, HISTORY, previous, prior, precedent, preceding, yesterday, yesteryear, the good
  old days, former, bygone, bypass, before
TRADITIONS, CUSTOMS, customary, conventional, established, ancestral, heritage, inherited,
  cultural, legacy, past-proven ways, old-line, orthodox, politically on the RIGHT AND
  REACTIONARY SIDE
HEALTH, LONG LIFE, LONGEVITY, YOUTHFUL, stamina, vitality, well-being, long-lasting,
  perennial, prolonged, protracted, continuing, extensive, extended, cure, lifelong, drawn-out
PESSIMISM, NEGATIVE, WORRY, ANXIETY, INSECURE, UNSURE, DOUBT, MISTRUST,
  SUSPICION, SKEPTICISM, QUESTIONING, UNCERTAIN, UNCERTAINTY, lowered
  expectations, serious minded, concern, disbelief, distraught, disturbed, hypochondria
INACTION, INACTIVITY, INDECISIVE, PASSIVE, apathetic, boredom, lazy, idleness, inertness,
  quiet, quiescence, sleep, asleep, sedentary, balk, dormant, lethargic, sluggish, static
INTROVERTED, WITHDRAWN, SHY, withdrawal, self-centered, detached, indifferent, demur,
  inner, within
PREDICTABILITY, PATIENCE, STABLE, MONOTONY, monotonous, forbearance, resignation,
  long-suffering, uncomplaining, composure, submissive, routine, tedious, with known results,
  the commonplace, the ordinary
STALEMATE, TIE, deadlock, hesitate, vaccillate, standoff
COMMONPLACE, DULL, BANAL, TRITE, BLAND, PROSAIC, stale, well-worn, worn-out,
  humdrum, clich'ed, "corny", platitudes, old, stereotyped, warmed-over

*A 90% REVERTIST DISLIKES OR FEARS THESE WORDS:*
THE PRESENT TIMES, NOW, NOWADAYS, TODAY, at once, immediately, right away, presently
THE FUTURE, TOMORROW, ANYTHING NEW, later, the times to come
OPTIMISM, POSITIVISM, anticipating the best, rose-colored glasses
EXTROVERSION, outside interests, external, overt
CHANGES, UNKNOWNS, UNCERTAINTIES, UNSETTLED TIMES, unstable, inconstant,
  alterations, modifications, mutations, variations, variance, deviation, diversity, differences,
  transformations, conversions, replacements, substitutions, exchanges
RISKS, CHALLENGES, THREATS, UNSAFE, INSECURITY, adventure, venture, excitement,
  danger, hazard, peril, gamble, chances, accident, dare, jeopardy, precarious, menace,
  vulnerable
TROUBLE, FAILURE, INJURY, STRESS, COMPLAINTS, distress, difficulty, harm, annoyance,
  hardship, predicament, inconvenience, strain, torment, trial, bother, disturbance,
  harrassment, irritant, sorrow, upset
ACTION, BUSY, IMPATIENCE, restless, hastiness, vigorous, animated, lively
UNCONVENTIONAL, INNOVATION, INVENTIVE, ORIGINAL, UNIQUE, UNUSUAL, creative,
  new, novel, novelty, imaginative, distinctive, strange, fresh, imported
ILLNESS, ILL HEALTH, UNHEALTHY, SICKNESS, DISEASE, PAIN, PAINFUL, CRAZINESS,
  ailment, affliction, debility, infirmity, plague, feebleness
SHORT-LIVED, EPHEMERAL, MOMENTARY, TRANSITORY, PASSING, briefly, abbreviated,
  curtailed, diminished, decreased, inadequate, insufficient Page 6

*"E" MEANS ENDURISM, A 90% ENDURIST LOVES THESE WORDS:*

PEACE OF MIND, MEDITATION, CONTEMPLATION, no worries or fears, composed, cogitative, pensive, ponder, reflect, muse, hypnosis WILL-POWER, DISCIPLINE, CONTROL, SELF-CONTROL, ORDER, ORDERLINESS, self-mastery, self-restraint, resolute, steadfast, govern, decorum STOICISM, UNQUESTIONING, TOTALLY UNCONCERNED, DISPASSIONATE, WITHDRAWAL FROM WORLDLY AFFAIRS, NEEDING ABSOLUTELY NOTHING! reject, spurn, repudiate, insensible, unresponsive, unfeeling, heedless, resigned, subjugate, spartan, durable, ENDURANCE, EVENTUALLY, ULTIMATE POWER, FORTITUDE, persistence, persistent, stamina, indomitable, unassailable, suffer, bearing, enduring severe pain, facing terminal illness bravely and stoically, outlast, tough out ETERNAL LIFE, PERPETUAL, ETERNAL THINGS, immortality, an infinite and eternal existence, constant, lasting, endless, unending, unceasing, permanent, everlasting, never-ending, timeless ABSTRACT, SPIRITUAL, conceptual, inference, hypothetical, theoretical, transcendental, visionary, immaterial, nothingness, spirit FATALISM, PREDESTINATION, PREORDAINED, PREDETERMINED, faith, foreordained, submission, "written in the stars", resigned, acquiescence, doomed BEYOND THIS WORLDLY LIFE, BEYOND TIME, BEYOND SPACE, unearthly, otherworldly, unworldly, celestial GREATEST KNOWLEDGE, WISDOM, KNOWS EVERYTHING, CERTAINTY, certitude, unambiguous, definitely, definite, beyond any doubt, wise, sage, seer TOTAL SATISFACTION, satiated, content, fulfilled UNCHANGING, CHANGELESS, STABLE, STEADFAST, CONSISTENT, CONSISTENCY, UNVARYING, immutable, unalterable, steadfast, steady, regular, sameness, fixed, firm, solid, sound STUBBORN, INFLEXIBLE, RIGID, UNCOMPROMISING, TRUTH, MUST, AUTHORITARIANISM, DEMANDS, ACCEPT, ACCEPTANCE OF A SINGLE MORALISTIC AUTHORITY FIGURE, authoritative, dictatorial, involuntary, compulsory, mandatory, obligatory, unquestioning, unquestionable, dogmatic, principles, creed, cult, sect, doctrine, doctrinaire, obstinate, dominate, regimentation, regulate, supervise, command, coercion, enforced, headstrong, intractable, subjugation, subordination, subservience, undoubted, veritable, authentic, indubitable, imperatives, bound, unwavering, captive, enslaved, slave, slavish, unyielding, bullheaded, stiff-necked, set in one's ways, free from doubt, stubborn as a mule, unbending, strict, religious leaders, prophet, heavy-handed JUDGMENTAL, CORRECT, RIGHTEOUS, UPRIGHT, PROPER, morality, moralizing, virtue, holy, devout, godly, pius, mores, standards, didactic, preach, sermonize MAGIC, MYSTERY, MYSTIC, MIRACLES, SPIRITUAL, SUPERNATURAL, METAPHYSICS, SOUL, RELIGION, RELIGIOUS, GOD, RITUALS, supernormal, conjure, incantations, sorcery, exorcism, church, prayer, faith, faithful, beliefs, believers, metaphysical, supernatural, divine, saintly, devout, sacred, holy, pius, church, heaven, hell, divining, devils, deviltry, Satan, satanism, witchcraft, bewitched, legerdemain, fortune-telling, occult, occultism, cryptic, obscure, soothsayer, voodoo, unknowable, incomprehensible, impenetrable, baffling, perplexing, enigma, riddle, puzzle, inscrutable, cabalistic, esoteric,

*A 90% ENDURIST WOULD HATE OR TRY TO AVOID THESE WORDS:*

ADAPTATION, FLEXIBILITY, VERSATILE, COMPROMISE, CHANGEABLE, fickle, inconstant, unstable, variable, varying, resilient, pliable, well-suited, transform, adjust, capricious, adjust, shift, fit, tailor-made, acclimate, malleable, many-sided

FREE-WILL, CHOICES, INDEPENDENCE, preferences, free, freedom, rights, options, liberated, emancipated, emancipation, democratic, democracy, self-rule, self-governing,

DISORDER, DISORGANIZED, INCONSISTENT, INCONSISTENCY, SIN, CHAOS, CONFUSION, disarray, upset, unsettled, unstable, anarchy, rebellious, unrestrained, irregular, irregularities, commotion, disrupt, disruption, tumult, turmoil, unfettered, inconstancy, disturb, disturbance, protest, riot, disintegration, worry, struggle, problems, topsy-turvey, unhinged, mixed-up

(WORLDLY) DESIRES, NEEDS, WANTS, REQUIREMENTS, WISHES, HOPES, cravings, covet, hunger, longing, yearning, greed, wrong, likes, requests, thirst, pining

WORLDLY, MATERIALISM, ungodly, godless, irreligious, mundane, temporal, carnal, corporeal, material, concrete, earthy, earthly,

THIS LIFE AND HUMAN BEINGS, PERSONAL INVOLVEMENT, personal entanglement

UNBELIEF, DISBELIEF, SKEPTICISM, QUESTIONABLE, QUESTIONING, DOUBT, DISTRUST, DEBATE, DISPUTE, UNCERTAIN, UNCERTAINTY, UNSURE, INCREDULITY, WHY? intellect, objections, inquisitive, irresolute, unresolved, curiosity, challenge, uncertitude, problematical, dubious, mistrust, arguable, argument, obscure, vague, repudiate

RATIONAL, RATIONALE, REASONING, FACTS, LOGIC, SCIENCE, REALITY, objectivity, sensible, justification, deduce, inquiry, explanation, rationalization, ambiguity, straightforward, lucid, common sense

FLEETING, TRANSIENT, TRANSITORY, ephemeral, momentary, short-lived, volatile Page 8

*a. "O" REFERS TO <u>CENTRISM</u>, THE HYBRID TOTAL MIXTURE OF ALL THE BEST PARTS FROM THE OTHER FIVE PHILOSOPHIES. A PERSON WHO FOLLOWS CENTRISM WOULD HAVE A PREFERENCE FOR THESE WORDS:*

ALL THE BASIC PREFERENCES FROM ALL FIVE WAYS OF LIFE -- INCLUDING CAREFREE PLAY, COOPERATIVE LOVE, COMPETITIVE WORK, CAREFUL SECURITY, CONTEMPLATIVE SOUL, <u>AND</u> LIFE ITSELF!

FREE, FREEDOM, VOLUNTARY
MODERATE, UNEXCESSIVE, NOT EXCESSIVE, ENOUGH, TEMPERATE, temperance, level-headed, adequate, sufficient, discreet, modest
HARMONY, COMPROMISING, REASONABLE, APPROPRIATE, JUST, JUDICIOUS, IMPARTIAL, TOLERANT, EQUITABLE, OPEN-MINDED, UNBIASED, UNPREJUDICED, OBJECTIVE, FAIR, tolerably, constrained, forbearance, fairly, fair and square, sportsmanlike, nondiscriminatory, prudent, integrate, intermediate, even, equitable, more or less, sort of
MODERATION, THE GOLDEN MEAN, MIDDLE-OF-THE-ROAD, HAPPY MEDIUM, middle-way
CHOICES, OPTIONS, CHANGING OPINIONS, EVALUATE, DECIDING, alternatives, preferences, prerogatives, discretion, select, selections, determine, assess, appraise, pick
APPROPRIATE, SUITABLE, VALID, apt, applicable, befitting, fit, fitting, suitable, pertinent, relevant, acceptable, expedient, timely, compatible, desirable, worthy, justified, down-to-earth, matter-of-fact, connected
DELIBERATE, DEBATE, ARGUE, ARGUMENTS, DISPUTE, ANALYZE, controversy, contend, contention, judge, adjudicate, dialectic, rhetoric, conjecture, investigate, analyze, scrutinize, resolve, surmise, resolve, make up one's mind
COMMON SENSE, WISDOM, SENSIBLE, SANE, "NORMAL", making sense, discerning, good judgment, horse sense, insight, sage, sagacity, perspicacity
EQUILIBRIUM, COMPOSURE, BALANCED, WELL-BALANCED, strike a balance, "cool", dispassionate

*b. A 90% CENTRIST WOULD DISLIKE THESE WORDS:*

THE WORST EXCESSES OF ALL FIVE WAYS OF LIFE-- DANGER, BETRAYAL, SELFISHNESS, INTROVERSION, AND UNCOMPROMISING

EXCESS, EXCESSIVE, EXCESSIVENESS, EXTREMES, EXTREMIST, FANATICAL, intemperate, intemperance, indulgent, self-indulgent, radical, immoderate, farfetched, unconstrained, profligate, extravagant, exotic
UNFAIR, unjust
HATE, GREED
ILLOGICAL, UNREASONABLE, BIAS, PREJUDICED, DISCRIMINATORY, CLOSED-MINDED, IRRATIONAL, ABSURD, FOOLISH, NONSENSE, injudicious, unsound, unwise, unconnected, asinine, ultra, folly
STUBBORN, INFLEXIBLE, RIGID, UNCOMPROMISING, TRUTH, MUST, AUTHORITARIANISM, DEMANDS, ACCEPT, ACCEPTANCE OF A SINGLE MORALISTIC AUTHORITY FIGURE, authoritative, dictatorial, involuntary, compulsory, mandatory, obligatory, unquestioning, unquestionable, dogmatic, principles, creed, cult, sect, doctrine, doctrinaire, obstinate, dominate, regimentation, regulate, supervise, command, coercion, enforced, headstrong, intractable, subjugation, subordination, subservience, undoubted, veritable, authentic, indubitable, imperatives, bound, captive, enslaved, slave, slavish, unyielding, bullheaded, stiff-necked, set in one's ways, stubborn as a mule, unbending, strict, religious leaders, prophet, heavy-handed
DISHARMONY, UNBALANCED, IMBALANCE, INSANE, CRAZED, CRAZY, DEMENTED, DERANGED, LUNATIC, NUTS, unstable, mad, batty, C Copyright 1992 Aaron H. Shovers Appendix B

8

Again, it is necessary to repeat that each of these six Pathways is based upon an equally appealing and equally valuable Value System; any "normal" person would desire ALL of these rewards. Over the long-term, ALL of these paths are equally good, but no single one of them is ALWAYS PERFECT for all people. We have described all the most valuable BENEFITS that each Way of Life offers to us, and then we have delineated the horrible HAZARDS which are always to be found at the furthest extremes of each philosophy. No single pathway has all the best answers for all the problems in our world, because the farthest excesses of each of these beautiful roads ends up in a terrible trap!

EVERYTHING YOU DO INVOLVES OTHER PERSONS, INCLUDING ALL KINDS OF DIFFERENT PEOPLE FROM VARIOUS CULTURAL BACKGROUNDS. AND EACH TYPE OF PERSON YOU ENCOUNTER REQUIRES A TOTALLY DIFFERENT RESPONSE FROM YOU. IF YOU WISH TO COMMUNICATE WELL AND DEAL EFFECTIVELY WITH ALL SORTS OF PEOPLE (BE IT BUYING FOOD, SELLING SOAP, BORROWING MONEY, OR GETTING MARRIED), YOU MUST INTUITIVELY HAVE SOME IDEA, BOTH WHERE YOU ARE "AT" AND WHERE HE OR SHE IS "AT". TO ACCOMPLISH THIS ART FORM, YOU MUST FIRST BECOME AWARE OF ALL THINGS THAT DIVERSE HUMAN BEINGS PERCEIVE TO BE VITALLY IMPORTANT TO THEM. THEN, BY FOCUSING IN UPON CERTAIN KEY WORDS WHICH OBVIOUSLY TURN A SPECIFIC INDIVIDUAL "ON" OR "OFF", YOU CAN COMPREHEND HIS LIKES AND DISLIKES, OR EXACTLY WHERE THAT INDIVIDUAL IS PRESENTLY "AT".

(Take note of how a "key word" that is loved, favored, or not offensive to one Way of Life becomes hated, disinteresting, or unimportant to another philosophy. In this manner, all six of Polarism's philosophies align themselves up into THREE GROUPINGS OF DUAL PAIRS, with Mutulism versus Competism, Novism counteracting Revertism, and Endurism opposing Centrism! In other words, what is seen as lovable, desirable, important, or pleasant to one person can actually be hateful, fearful, unimportant, or repulsive to some one else):

9

IT'S MUTULISM VERSUS COMPETISM!

A MUTULIST IS INFATUATED WITH THESE WORDS; TO A COMPETIST, THESE THINGS WOULD BE HATEFUL, DISINTERESTING, OR UNIMPORTANT: <u>HUMAN BEINGS, "WE", FRIENDS, FAMILY, DEPENDABLE, RELIABLE, SOCIABLE, COMMUNICATE, CONSIDERATE, RESPECT, COOPERATION, LOVING OTHERS, TRUST, FEELINGS, EMOTIONS, SELF-IMAGE.</u>

A COMPETIST YEARNS FOR THESE OR FEELS THAT THEY ARE NOT OFFENSIVE; A MUTULIST FINDS THESE THINGS TO BE HATEFUL, DISINTERESTING, OR NOT IMPORTANT: <u>HERE-NOW NEEDS, SCIENCE, SURVIVAL, TANGIBLES, MATERIALISM, BODY-IMAGE, CAREER, WEALTH, INDEPENDENCE, ALONE, LONELINESS, HATE, INDIVIDUALISM, SELF-RELIANCE, SECLUSION, "I", SECRETS, WORK, COMPETITION, OPPORTUNITY, OPPORTUNISM, CAPABLE, SELFISHNESS, EVIL PEOPLE, BETRAYAL, AND BLAMING OTHERS.</u>

10

IT'S NOVISM OPPOSING REVERTISM!

A NOVIST RELISHES THESE WORDS; A REVERTIST WOULD DETEST THESE SAME THINGS: ANYWHERE, ANYTIME, HOPES, OPTIMISM, SUCCESS, INVINCIBLE, PLAY, FUN, THRILLS, RISK, HAZARDS, DANGER, UNPREDICTABILITY, ADVENTURE, CHALLENGES, DISCOVERY, CURIOSITY, CAREFREE, INTUITION, SPONTANEOUS, UNPLANNED, ACTION, REBELLION, NONCONFORMITY, SEDUCTIVE, SEX, FICKLE, IMPETUOUS, EXTROVERT, DIFFERENT, BIZARRE, INVENTIVE, NOVEL, AND INNOVATIVE.

A REVERTIST WOULD FIND THESE THINGS TO BE SIGNIFICANT; NOVISTS WOULD BE MOST UNCONCERNED ABOUT SUCH THINGS, OR EVEN HATE THEM: FAILURE, THE PAST-PROVEN WAYS, PESSIMISM, PROBLEMS, FEARS OF ANY KIND, TROUBLE, AVOIDING TROUBLE, CONFORMITY, THE STATUS QUO, ADVERSITY, LOWERED EXPECTATIONS, TRADITIONS, HISTORY, FAMILIAR THINGS, PREDICTABILITY, STABILITY, MISTAKES, INACTIVITY, QUIET LIFE, ROUTINE, BOREDOM, INTROVERTED, YOUTHFUL, LONG LIFE, HEALTH, SICKNESS, CAREFULNESS, CAUTIOUS, PROTECTION, SAFE, SECURITY, PATIENCE.

11

THIS IS ENDURISM FIGHTING CENTRISM!

AN ENDURIST WOULD BELIEVE THAT THESE WORDS ARE DESIRABLE, IMPORTANT, OR PLEASANT; A CENTRIST WOULD FIND THESE SAME THINGS TO BE HATEFUL, FEARFUL, REPULSIVE, OR NOT IMPORTANT: <u>PERFECTION</u>, <u>PREDESTINATION</u>, <u>FATE</u>, <u>STRONG PRINCIPLES</u>, <u>ABSOLUTISM</u>, <u>DISPUTED TRUTH</u>, <u>EXCESSES</u>, <u>EXTREMES</u>, <u>AUTHORITARIANISM</u>, <u>TOTALITARIANISM</u>, <u>ORDERLY</u>, <u>FOREVER</u>, <u>ETERNITY</u>, <u>INFINITY</u>, <u>BEYOND TIME</u>, <u>BEYOND SPACE</u>, <u>ABSTRACTIONS</u>, <u>SPIRITUAL</u>, <u>MAGIC</u>, <u>MYSTERY</u>, <u>RELIGION</u>, <u>GOD</u>, <u>HEAVEN</u>, <u>HELL</u>, <u>NOTHINGNESS</u>, <u>STOICISM</u>, <u>IGNORE WORLDLY THINGS</u>, <u>MEDITATION</u>, <u>WITHDRAWAL</u>, <u>ENDURANCE</u>, <u>UNCOMPROMISING</u>, <u>COMMITMENT</u>, <u>BELIEFS</u>, <u>EXCLUSIVE BELIEFS</u>, <u>SOUL</u>, <u>PEACE OF MIND</u>, <u>THE STATUS QUO</u>, <u>CONFORMITY</u>, <u>SATISFACTION</u>, <u>CONTROL</u>, <u>DISCIPLINE</u>, <u>INFLEXIBLE</u>, <u>STUBBORN</u>, <u>JUDGMENTAL</u>, <u>BIASED</u>, <u>CERTAINTY</u>, <u>SIN</u>, <u>DEVILS</u>, <u>WILLPOWER</u>, AND <u>DEATH</u>.

A CENTRIST CHERISHES ALL THESE; AN ENDURIST WOULD SEE THESE SAME THINGS AS HATEFUL, FEARFUL, REPULSIVE, OR NOT IMPORTANT: <u>MODERATION</u>, <u>REASONABLE</u>, <u>RELEVANT</u>, <u>USEFUL</u>, <u>APPROPRIATE</u>, <u>FAIR</u>, <u>COMPROMISE</u>, <u>FREE-WILL</u>, <u>ADAPTABLE</u>, <u>CHOICES</u>, <u>ALTERNATIVES</u>, <u>OPTIONS</u>, <u>DECISIONS</u>, <u>PLANNING</u>, <u>RELATIVISM</u>, <u>JUDGING</u>, <u>NEGOTIATE</u>, <u>DIVERSE OPINIONS</u>, <u>PLURALISM</u>, <u>DEPENDING ON THE CIRCUMSTANCES</u>, <u>NONCONFORMITY</u>, <u>ALL DESIRES</u>, <u>ALL NEEDS</u>, <u>ALL OF LIFE</u>, <u>THE WORLD</u>, <u>THE EARTH</u>, <u>DEMOCRATIC</u>, <u>CHANGING TIMES</u>, <u>CHANGING OPINIONS</u>, <u>ANALYZING</u>, <u>ARGUING</u>, <u>DEBATE</u>, <u>QUESTIONS</u>, <u>RIDDLES-PUZZLES</u>, <u>ANSWERS-SOLUTIONS</u>, <u>LOGIC</u>, <u>REASONING</u>, <u>EDUCATION</u>, <u>LEARNING</u>, <u>DEEP THINKING</u>, <u>WISDOM</u>, <u>BRAIN POWER</u>, <u>OPEN-MINDEDNESS</u>, <u>UNBIASED</u>, <u>WORRY</u>, <u>STRUGGLE</u>, <u>DISORDERLINESS</u>, <u>UNDISCIPLINED</u>, <u>WORLDLY NEEDS</u>, <u>WORLDLY INVOLVEMENT</u>, AND <u>LONG-TERM FULFILLMENT</u>.

12

THE GAME OF MAGIC WORDS

Each human brain picks and chooses certain "key words" which have proven over time to best express one's FAVORITE THINGS, as well as a person's MOST HATED THINGS. Thus, by focusing in on the way an individual uses these words, it becomes possible to figure out exactly where that person is "at", what is important to him, and just about what he will be doing next!

These words are listed in alphabetical order. They are followed by the Shovers Philosophy Index: "N" refers to Novism, "R" means Revertism, "M" stands for Mutulism, "C" is the philosophy of Competism, and "O" points us to the Centrism Way of Life.

Because most of these words can be used to express more than one Way of Thinking, we must also categorize according to the CONTEXT of "How this specific word was used by the person". If the context reflects that the person finds this word LOVABLE, DESIRABLE, PLEASANT, OR IMPORTANT, the first letter, a CAPITAL LETTER, indicates his philosophy of life. When the word usage expresses HATRED, FEAR, REPULSIVENESS, OR UNIMPORTANCE, a subsequent SMALL LETTER indicates his belief systems. For example, the word "adaptable" used in a favorable manner belongs to a Centrist, but the same word used in an unfavorable way demonstrates that the speaker is an Endurist. A Competist LOVES being alone; a Mutulist HATES it.

ABSOLUTISM Eo
ABSTRACTIONS Eo
ACTION Nr
ADAPTABLE Oe
ADVENTURE Nr
ADVERSITY Rn
ALL NEEDS Oe
ALL DESIRES Oe
ALL OF LIFE Oe
ALONE Cm
ALTERNATIVES Oe

13

AN IMPROVED FUTURE Mc
ANALYZING Oe
ANSWERS-SOLUTIONS Oe
ANYTIME Nr
ANYWHERE Nr
APPROPRIATE Oe
ARGUING Oe
AUTHORITARIANISM Eo
AVOIDING TROUBLE Rn
BELIEFS Eo
BETRAYAL Cm
BEYOND SPACE Eo
BEYOND TIME Eo
BIASED Eo
BIZARRE Nr
BLAMING OTHERS Cm
BODY-IMAGE Cm
BOREDOM Rn
BRAIN POWER Oe
CAPABLE Cm
CAREER Cm
CAREFREE Nr
CAREFULNESS Rn
CAUTIOUS Rn
CERTAINTY Eo
CHALLENGES Nr
CHANGING OPINIONS Oe
CHANGING TIMES Oe
CHOICES Oe
COMMITMENT Eo
COMMUNICATE Mc

14
COMPETITION Cm
COMPROMISE Oe
CONFORMITY Rn
CONSIDERATE Mc
CONTROL Eo
COOPERATION Mc
CURIOSITY Nr
DANGER Nr
DEATH Eo
DEBATE Oe
DECISIONS Oe
DEEP THINKING Oe
DEMOCRATIC Oe
DEPENDABLE Mc
DEPENDENT Mc
DEPENDING ON THE CIRCUMSTANCES Oe
DEVILS Eo
DIFFERENT Nr
DISCIPLINE Eo
DISCOVERY Nr
DISORDERLINESS Oe
DIVERSE OPINIONS Oe
EDUCATION Oe
EMOTIONS Mc
ENDURANCE Ec
ETERNITY Eo
EVIL PEOPLE Cm
EXCESSES Eo
EXCLUSIVE BELIEFS Eo
EXPLANATIONS Oe
EXTREMES Eo

EXTREMISM Eo
EXTROVERT Nr
FAILURE Rn
FAMILIAR THINGS Rn
FAMILY Mc
FATE Eo
FEARS Rn
FEELINGS Mc
FICKLE Nr
FIRM, RIGID Eo
FOREVER Eo
FREE-WILL Oe
FRIENDS Mc
FUN Nr
GOD Eo
HATE Cm
HAZARDS Nr
HEALTH Rn
HEAVEN Eo
HELL Eo
HERE-NOW NEEDS Cm
HISTORY Rn
HOPES Nr
HUMAN BEINGS Mc
HUMAN NATURE Mc
"I" Cm
IGNORE WORLDLY THINGS Eo
IMPARTIAL-FAIRNESS Oe
IMPETUOUS Nr
INACTIVITY RN
INDEPENDENCE Cm

16
INDIVIDUALISM Cm
INFINITY Eo
INFLEXIBLE Eo
INNOVATIVE Nr
INTROVERTED Rn
INTUITION Nr
INVENTIVE Nr
INVINCIBLE Nr
JUDGING Oe
JUDGMENTAL Eo
LEARNING Oe
LOGIC Oe
LONELINESS Cm
LONG LIFE Rn
LONG-TERM FULFILLMENT Oe
LOVING OTHERS Mc
LOWERED EXPECTATIONS Rn
MAGIC Eo
MATERIALISM Cm
MEDITATION Eo
MISTAKES Rn
MODERATION Oe
MYSTERY Eo
NEGOTIATE Oe
NONCONFORMITY Nr
NOTHINGNESS Eo
NOVEL Nr
OPEN-MINDEDNESS Oe
OPPORTUNISM Cm
OPPORTUNITY Cm
OPTIMISM Nr

OPTIONS Oe
ORDERLINESS Eo
ORDERLY Eo
PATIENCE Rn
PEACE OF MIND Eo
PERFECTION Eo
PESSIMISM Rn
PLANNING Oe
PLAY Nr
PLURALISM Oe
PREDESTINATION Eo
PREDICTABILITY Rn
PROBLEMS Rn
PROTECTION Rn
QUESTIONS Oe
QUIET LIFE Rn
REASONABLE Oe
REASONING Oe
REBELLION Nr
RELATIVISM Oe
RELEVANT Oe
RELIABLE Mc
RELIGION Eo
RESPECT Mc
RIDDLES-PUZZLES Oe
RISK Nr
ROUTINE Rn
SAFE Rn
SATISFACTION Eo
SCIENCE Cm
SECLUSION Cm

18
SECRETS Cm
SECULAR THINGS Oe
SECURITY Rn
SEDUCTIVE Nr
SELF-IMAGE Mc
SELF-RELIANCE Cm
SELFISHNESS Cm
SEX Nr
SICKNESS Rn
SIN Eo
SOCIABLE Mc
SOUL Eo
SPIRITUAL Eo
SPONTANEOUS Nr
STABILITY Rn
STOICISM Eo
STRONG PRINCIPLES Eo
STRUGGLE Oe
STUBBORN Eo
SUCCESS Nr
SURVIVAL Cm
TANGIBLES Cm
THE PAST-PROVEN WAYS Rn
THE STATUS QUO Rn
THE EARTH Oe
THE WORLD Oe
THE FUTURE Mc
THE PRESENT TIMES Cm
THRILLS Nr
TOTALITARIANISM Eo
TRADITIONS Rn

TROUBLE Rn
TRUST Mc
UNBIASED Oe
UNCOMPROMISING Eo
UNDISCIPLINED Oe
UNDISPUTED TRUTH Eo
UNPLANNED Nr
UNPREDICTABILITY Nr
USEFUL Oe
"WE" Mc
WEALTH Cm
WILLPOWER Eo
WISDOM Oe
WITHDRAWAL Eo
WORK Cm
WORLDLY INVOLVEMENT Oe
WORLDLY NEEDS Oe
WORRY Oe
YOUTHFUL Rn

Page 1 a. <u>A 90% NOVIST LOVES THESE WORDS</u> (in the context of Carefree, nonchalant):

b. A 90% REVERTIST HATES THE SAME WORDS:

OPTIMISM, POSITIVISM, HOPES, hopeful, anticipating the best, upbeat, wearing rose-colored glasses CAREFREE, CARELESS, IMPETUOUS, IMPULSIVE, IMPATIENT, IMPATIENCE, UNPLANNED, SPONTANEOUS, SHORT-LIVED, EPHEMERAL, MOMENTARY, TRANSITORY, PASSING, FLEETING, TRANSIENT, temperamental, erratic, restless, hastiness, briefly, abbreviated, fickle, inconstant, unstable, impromptu, presently, mercurial, happy-go-lucky, foolhardy, license, improvised, spur of the moment, offhand, capricious, careless, vacillating, curtailed, politically on the RADICAL side, SEX, procreate, propagate, reproduction, erotic, lust, spicy, risque, racy, suggestive, exotic FEARLESS, INVINCIBLE, UNLIMITED, POTENT, AUDACIOUS, COURAGE, POWER, POWERFUL, invulnerable, unbeatable, strong, strength, indomitable, brave, unafraid, valiant, mighty, tough, over-confident, untouchable, daring, cocky, cock-sure ADVENTURE, CHALLENGES, DANGER, ANYWHERE, ANYTIME, RISKS, THREATS, UNSAFE, INSECURITY, ventures, hazards, peril, gamble, chances, reckless, adversity, exploits, accident, dare, jeopardy, precarious, menace, quest EXCITEMENT, PLAY, thrills, entertainment, stimulation, fascinating, intriguing, enthralling EXTROVERT, EXTROVERSION, outside interests, external, overt, outwardly-oriented NONCONFORMITY, UNCONVENTIONAL, INNOVATION, INVENTIVE, ORIGINAL, UNIQUE, NEW, NOVEL, UNUSUAL, INGENIOUS, CREATIVE, CURIOUS, CURIOSITY, UNBALANCED, IMBALANCE, INSANE, CRAZED, CRAZY, CRAZINESS, DEMENTED, DERANGED, LUNATIC, NUTS, mad, batty, unorthodox, novelty, imaginative, distinctive, strange, oddity, peculiar, bizarre, fresh, imported (in the context of "Carefree, without thought, nonchalant" - see O)
ADAPTATION, ACCOMODATE, FLEXIBILITY, VERSATILE, COMPROMISE, COORDINATE, CHANGES, CHANGEABLE, CHANGING TIMES, ANYTHING NEW, UNPREDICTABLE, UNKNOWNS, UNCERTAINTY, UNCERTAINTIES, UNSETTLED TIMES, variable, varying, variations, variance, reconcile, reconciliate, resilient, pliable, well-suited, alterations, modifications, mutations, deviation, diversity, differences, unplanned, spontaneous, extemporaneous, unsureness, transformations, conversions, replacements, substitutions, exchanges

(in the context of neutral or "Carefree, without thought, nonchalant" - see O)
UNDISCIPLINED, IRRESPONSIBLE, UNRELIABLE, NOT DEPENDABLE, REBELLING, ANARCHY, STRESS, DISORGANIZED, DISHARMONY, INCONSISTENT, INCONSISTENCY, CHAOS, CONFUSION, disarray, upset, unsettled, insurgent, mutiny, lawlessness, rebellious, unrestrained, irregular, irregularities, commotion, disrupt, disruption, tumult, turmoil, volatile, unfettered, disturbed, disturbance, protest, riot, disintegration, struggle,

Page 2 problems, topsy-turvey, unhinged, mixed-up

(in the context of neutral or "being curious" - see O)
EDUCATION, KNOWLEDGE, learn, learning, informed, enlightened, instruction, schooling, teaching, tutor

(in the context of neutral or "for fun and games" - see C)
ACTION, DOING, BUSY, dynamic, vigorous, animated, lively, activate, react, deeds, exploits, energize, arouse, vivacious, oomph

(in the context of neutral or "for fun and excitement - see O)
LIFE, LIFE-ORIENTED, alive, lively, buoyant, effervescent

(in the context of "to the highest degree" - see C)
SELF-ESTEEM, SELF-ASSURANCE, CAPABLE, ABLE, ABILITY, COMPETENT, COMPETENCE, QUALIFIED, confident, self-confident, effective, adept, tested, trained, proven, fit, able-bodied

(in the context of neutral or "physical", but "not mental" - see O)
DISCOVERY, EXPLORE, EXPLORATION, reveal, revelation, disclose, expose, aware, ascertain, determine, find out, detect, examine, observe, perceive a. A 90% REVERTIST PREFERS THESE WORDS:

b. A 90% NOVIST HATES THE SAME WORDS:

SAFE, SAFEGUARD, SECURE, SECURITY, PROTECTION, PRESERVATION, PREVENTION, AVOIDING COSTLY OR STUPID ACTIONS, CAREFUL, CAUTIOUS, wary, riskless, guard, defend, defense, safeguard, shelter, shield, limits, unhurt PAST TIMES, HISTORY, previous, prior, precedent, preceding, yesterday, yesteryear, the good old days, former, bygone, before CONFORMITY, TRADITIONS, CUSTOMS, customary, conventional, established, ancestral, heritage, inherited, cultural, legacy, old-line, past-proven ways, fit in, integrate, comply, orthodox, politically on the RIGHT AND REACTIONARY SIDE HEALTH, LONG LIFE, LONGEVITY, YOUTHFUL, stamina, vitality, well-being, long-lasting, perennial, prolonged, protracted, continuing, extensive, extended, cure, lifelong, drawn-out PESSIMISM, NEGATIVE, WORRY, ANXIETY, INSECURE, DEFEATISM, MISTRUST, IMPOTENT, HOPELESSNESS, weak, weakness, decrepit, feeble, feebleness, frail, debilitated, inferior, powerless, defeatism, despair, gloom, lowered expectations, serious minded, concern, worrywarts, distraught, disturbed, FAILURE, LOSE, LOSING, GIVING UP, SURRENDER, RESIGN, MISTAKES, ERROR, blunder, miscalculate, misinterpret, misjudge, confusion, disappoint, disappointment, thwart, preclude, block, hinder, impede, obstruct, obstruction, upset, mixed up, misconstrue, blooper, slipup, make a boo-boo, bungle, louse up, screw up INACTION, INACTIVITY, INDECISIVE, PASSIVE, BOREDOM, MONOTONY, THE STATUS QUO, static, idleness, quiet, sedentary, routine, tedious, tedium, dull, monotonous, familiar things, apathetic, lazy, laziness, inertness, sleep, asleep, quiescence, dormant, lethargy, dreary, drudging, tiresome, tiring, balk, sluggish PREDICTABLE, PREDICTABILITY, PATIENCE, STABLE, STABILITY, forbearance, resignation, long-suffering, uncomplaining, composure, with known results, INTROVERTED, WITHDRAWN, SHY, inhibited, subdued, submissive, restrained, withdrawn, demur, repressed, circumspect, discreet, inner, within STALEMATE, TIE, deadlock, hesitate, vaccillate, standoff COMMONPLACE, DULL, BANAL, TRITE, BLAND, PROSAIC, ordinary, stale, well-worn, worn-out, humdrum, clich'ed, "corny", platitudes, old, stereotyped, warmed-over TROUBLE, INJURY, ILLNESS, ILL HEALTH, UNHEALTHY, SICKNESS, DISEASE, PAIN, PAINFUL, STRESS, ailment, affliction, distress, difficulty, harm, annoyance, hardship, predicament, inconvenience, strain, hypochondria, torment, trial, bother, disturbance, harrassment, irritant, sorrow, upset, debility, infirmity, plague,

(in the context of "referring to one's own self" - see C)

BLAME, CRITICIZE, CRITICISM, UNFAIR, UNJUST, GREED, GREEDY, TREACHERY, TRAITOROUS, TREASON, underhanded, sneaky, devious, condemn, ostracize, denounce, accuse, reproach, fault, knock, censure, impeach, exile, expel, expulsion, banish, throw out, deport, guilt feelings, delinquent, tricky, informers, squealers, stool pigeon, talebearer, tattler, tattletale a. A 90% MUTULIST IDEALIZES THESE WORDS:
b. A 90% COMPETIST DISLIKES THESE SAME WORDS:

LOVE, LOVING, LOVABLE, CONCUR, approval, accord, affection, benevolent, humanitarian, compatible, congenial, rapport, charitable, altruism, likable, genial, cordial, good-natured, dote, devotion WE, FRIENDS, FAMILY, friendly, children, sociable, coexist, unite, ally, companion, mate, gregarious, associates, relationships, tribe, community, society, fellowship, club, fraternity, sorority, concord, accompanied, home, other persons, people, the public HUMANITY, HUMANS, mankind, Man (in the generic sense, including women), contemporaries TRUST, TRUSTWORTHY, RELIABLE, HONEST, justice, dependable, responsible, duty, faithful, humane, righteous, upright, honorable, decent, good, high-principled, entrust, ethics, manners COOPERATION, COOPERATIVE, NONCOMPETITIVE, AGREE, AGREEMENT, AGREEABLE, collaborating, harmonize, serve, synergism, concur, in concert, politically a "bleeding heart" LIBERAL RESPECT, RESPECTABLE, PRAISE, COMPLIMENT, self-image, acceptance, status, esteem, commend, acclaim, admire, applause DEPENDENT, DEPENDENT UPON OTHERS, FINANCIAL DEPENDENCE, RELIANT, RELIANCE, LOSS OF CONTROL, INCAPACITY, VULNERABLE, relying on others, yield, relinquish, incapable, inability, inadequate, ineffective, ineffectual, not effective, unqualified, poor, impoverished, unemployed, indigence, destitution, going broke, terminated, welfare, privation EMOTIONS, EMOTIONAL, FEELINGS, SENSITIVE, sentimental, softhearted, responsive, Page 4 responsiveness, warmth, romantic, sympathetic, kind, kindhearted, considerate, compassionate, understanding, the needs of other people, passion, dreamy, starry-eyed, poetry, art, arty, artistic DISORGANIZED, UNORGANIZED, UNPLANNED, IMPRACTICAL, UNREALISTIC, idealistic, visionary, ivory-tower, aimless, haphazard, hit-or-miss, unintentional, inadvertent, random TALK, TALKATIVE, VOCAL, communicating with other people, outspoken, openness DISSATISFIED, DISCONTENTED, COMPLAINTS, FRUSTRATIONS, disgruntled, malcontent, ungratified, politically on the LEFT THE FUTURE, FUTURE, TOMORROW, LATER, high expectations, an improved future, afterwards, the times to come a. A 90% COMPETIST WOULD SELECT THESE WORDS:

b. A 90% MUTULIST HATES THESE SAME WORDS:

SELF-RELIANCE, SELF-SUFFICIENT, INDEPENDENCE, INDEPENDENT, "I", INDIVIDUAL, INDIVIDUALISM, LONELINESS, LONELY, ALONE, LONESOME, egocentric, self-centered, solitary, abandoned, deserted, forsaken, isolated, self-made, self-supported, privacy, personal, sovereign, autonomous, on one's own, alienation, disintegration, estrangement, single, singular, solo, separate, separated, selfish MATERIALISM, TANGIBLES, REALISM, REALITY, REAL, OBJECTS, OBJECTIVE, SCIENCE, SCIENTIFIC, CONCEPTS, FACTS, profit, things, house, food, car, appliances, devices, physical, entity, concrete, actual, actually, actuality, components, parts, factors, elements, ingredients, apparatus, equipment, machine, gear, outfits, clothing, matter-of-fact, palpable, perceptible, embody, paraphernalia, stuff, redundancy, substance, substantially, animal, carnal, body, body image (skin, muscles, fat)

FACTS, LOGIC, LOGICAL, ORGANIZE, WELL-ORGANIZED, SYSTEMS, SYSTEMATIC, SYSTEMATIZE, PLAN, PLANNING, PLANNED, methods, methodical, calculating, analytical, design, designing, strategy, obvious, self-evident, pertinent, fundamental, basic, valid, applicable, straightforward, clear, proof, germane, manifest, plain, lucid, well thought out, with a game plan IMPERSONAL, UNEMOTIONAL, detached, reserved, unfeeling, cold, cold-blooded NOT TALKATIVE, CONFIDENTIAL, CONFIDENTIALITY, SILENCE, SECRET, SECRETIVE, QUIET, concealment, hush-hush, clandestine, covert, sly, subterfuge, subrosa, undercover, hidden, behind closed doors, on the Q.T., under the table, politically CONSERVATIVE WIN, TRIUMPH, VICTORY, GAIN, PROFIT, ACCOMPLISH, ACHIEVE, ACHIEVEMENT, acquire, control, superiority, supremacy, overcome, outwit, prevail, victory, dominate, dominant, earn BETRAYAL, DECEIVED, HATE, DESPISE, DETEST, LOATHE, EVIL PEOPLE, resent, resentful, repulsive, malicious, viscious, horrible, horrid, mean, obnoxious, contemptible, deluded, misleading, dishonest, double-crossed, disloyal, sold out, taken in, despicable, reprehensible, repugnant, revulsion, nasty, spiteful, scorn, disdain, dislike, detest, evil, enmity, odious, aversion, abhor, vile, hostility, bitchy, catty, infidelity, beguiled, sold down the river, broke faith, unfaithful, faithless OPPORTUNITY, OPPORTUNISTIC, well-timed, auspicious, an opening, a good break, a good chance for success, promising circumstances, the favorable time and the proper occasion Page 5

WEALTH, WEALTHY, RICH, PROSPERITY, FINANCIAL INDEPENDENCE, affluence, abundance, financial well-being, economic prosperity, riches, surplus, superfluous
NOW, TODAY, IMMEDIATELY, RIGHT AWAY, the present times, nowadays, at once, instantly HERE, IN THIS WORLD, WORLDLY, SECULAR, DURING THIS LIFETIME, earthly, down-to-earth, in this place, in this vicinity, mundane, temporal
(in the context of neutral or "referring to other people, not one's self" - see R)
BLAME, CRITICIZE, CRITICISM, UNFAIR, UNJUST, GREED, GREEDY, TREACHERY, TRAITOROUS, TREASON, underhanded, sneaky, devious, condemn, ostracize, denounce, accuse, reproach, fault, knock, censure, impeach, exile, expel, expulsion, banish, throw out, deport, guilt feelings, delinquent, tricky, informers, squealers, stool pigeon, talebearer, tattler, tattletale
(in the context of neutral or "with tangible things" - see O)
PRACTICAL, PRAGMATIC, functional, workable, useful, utilitarian, constuctive, applicable, feasible, implicit,
(in the context of neutral or "for quick tangible gains" - see O)
WORK, JOB, OCCUPATION, CAREER, training, instruction, livelyhood, labor, business, employment, profession, trade, vocation, craft, chores, hard work, strive, toil, effort, make an effort, try, attempt, exertion, perform, handicraft, produce, procedures, process, operate, use, function
(in the context of neutral or "in the physical sense, for tangible gains" - see O)
COMPETE, COMPETITION, CONTROVERSY, FIGHT, QUARREL, contend, contention, antagonize, antagonism, conflict, competitor, rival, enemy, contest, aggression, battle, war, warfare, tug-of-war, struggle, animosity, exploit
(in the context of "for tangible gain" - see N)
ACTION, DOING, BUSY, dynamic, vigorous, animated, lively, activate, react, deeds, exploits, energize, arouse, vivacious, oomph
(in the context of neutral or "to a moderate degree" - see N)
SELF-ESTEEM, SELF-ASSURANCE, CAPABLE, ABLE, ABILITY, COMPETENT, COMPETENCE, QUALIFIED, confident, self-confident, effective, adept, tested, trained, proven, fit, able-bodied Page 6 a. A 90% ENDURIST LOVES THESE WORDS (all in the context of "to the highest degree"):

b. "O" MEANS CENTRISM; A 90% CENTRIST WOULD HATE:

THE WORST EXCESSES FROM ALL FIVE WAYS OF LIFE (DANGER, BETRAYAL, SELFISHNESS, INTROVERSION, AND UNCOMPROMISING RIGIDITY)
EXCESSES, EXCESS, EXCESSIVE, EXCESSIVENESS, EXTREMES, EXTREMIST, FANATICAL, intemperate, intemperance, indulgent, self-indulgent, radical, immoderate, ultra, farfetched, unconstrained, profligate, extravagant, exotic AUTHORITIES, AUTHORITARIANISM, CONTROL, authoritative, dictatorial, involuntary, compulsory, mandatory, obligatory, submission, govern, rulers, rules, leaders, laws, edicts, regulations, statutes, dominate, domination, bondage, slavery, subjugate, subjugation, regimentation, regulate, supervise, command, coercion, subordination, subservience, bound, captive, enslaved, slave, slavish, enforced, serfdom, commands, mandates FORCED, COMPELLED, COERCED, OBEDIENCE, OBEY, JUDGMENTAL, CORRECT, RIGHTEOUS, UPRIGHT, PROPER, morality, moralizing, virtue, holy, devout, godly, pius, mores, standards, didactic, preach, sermonize ORDER, ORDERLINESS, PEACE OF MIND, HARMONY, MEDITATION, CONTEMPLATION, composed, cogitative, pensive, ponder, reflect, muse, hypnosis WILL-POWER, DISCIPLINE, SELF-CONTROL, self-mastery, self-restraint, decorum STOICISM, UNQUESTIONING, TOTALLY UNCONCERNED, INDIFFERENT, NO WORRY, DISPASSIONATE, WITHDRAWAL FROM ALL WORLDLY AFFAIRS, FORTITUDE, NEEDING ABSOLUTELY NOTHING! reject, spurn, repudiate, insensible, unresponsive, unfeeling, heedless, resigned, spartan, durable ENDURE, ENDURANCE, EVENTUALLY, ULTIMATELY, SURVIVAL, outlive, outlast, persist, persistence, persistent, stamina, indomitable, unassailable, suffer, continue, exist, come through, pull through, carry on, enduring severe pain, facing terminal illness bravely and stoically, tough out ETERNAL LIFE, PERPETUAL, TIMELESS, ETERNAL THINGS, immortality, an infinite and eternal existence, constant, lasting, endless, unending, unceasing, permanent, everlasting, never-ending, timeless FATALISM, PREDESTINATION, PREORDAINED, PREDETERMINED, faith, foreordained, "written in the stars", resigned, acquiescence, doomed ILLOGICAL, UNREASONABLE, IRRATIONAL, ABSURD, FOOLISH, NONSENSE, injudicious, unsound, unwise, unconnected, unknowable, incomprehensible, impenetrable, baffling, perplexing, enigma, riddle, puzzle, inscrutable, obscure, folly, asinine ABSTRACT, ABSTRACTIONS, INTANGIBLE, SPIRITUAL, conceptual, inference, hypothetical, theoretical, transcendental, visionary, immaterial, symbolic, nothingness, esoteric BEYOND THIS WORLDLY LIFE, BEYOND TIME, BEYOND SPACE, SUPERNATURAL, UNREAL, unearthly, otherworldly, unworldly, celestial, supernormal, heavenly, death, deceased, demise, grim reaper, grave, fatal, lethal, corpse, cadaver, ghost, spirit MAGIC, MYSTERY, MYSTIC, MIRACLES, METAPHYSICS, METAPHYSICAL, SOUL, RELIGION, RELIGIOUS, GOD, RITUALS, conjure, incantations, sorcery, exorcism, prayer, faith, faithful, beliefs, believers, divine, saintly, devout, sacred, holy, pius, church, creed, cult, sect, heaven, hell, divining, devils, deviltry, Satan, satanism, witchcraft, bewitched, legerdermain, fortune-telling, occult, occultism, cryptic, soothsayer, voodoo, cabalistic, religious leaders, prophet GREATEST KNOWLEDGE, WISDOM, KNOWS EVERYTHING, CERTAINTY, certitude, unambiguous, definitely, definite, beyond any doubt, wise, sage, seer TOTAL SATISFACTION, satiated, content, fulfilled UNCHANGING, CHANGELESS, STABLE, STEADFAST, CONSISTENT, CONSISTENCY, UNVARYING, immutable, unalterable, steady, regular, sameness, fixed, firm, solid, sound STUBBORN, INFLEXIBLE, RIGID, UNCOMPROMISING, OBSTINATE, MUST, DETERMINED, DETERMINATION, ACCEPT, FIRMNESS, dogmatic, resolute, steadfast, headstrong, intractable, unwavering, unyielding, bullheaded, stiff-necked, set in one's ways, stubborn as a mule, unbending, strict, heavy-handed BIASED, PREJUDICED, DISCRIMINATORY, CLOSED-MINDED, ACCEPTANCE OF A SINGLE MORALISTIC AUTHORITY FIGURE, TRUTH, FIXED PRINCIPLES, unquestioning, unquestionable, doctrine, doctrinaire, undoubted, free from doubt, veritable, authentic, indubitable, imperatives, a. "O" REFERS TO CENTRISM, THE HYBRID MIXTURE OF ALL THE BEST PARTS FROM THE OTHER FIVE PHILOSOPHIES. A 90% CENTRIST WOULD PREFER THE FOLLOWING WORDS (in the context of "Moderation in all things"):

THE BASIC BENEFITS FROM ALL FIVE WAYS OF LIFE -- INCLUDING CAREFREE PLAY, COOPERATIVE LOVE, COMPETITIVE WORK, CAREFUL SECURITY, CONTEMPLATIVE SOUL, AND LIFE ITSELF b. A 90% ENDURIST WOULD HATE THESE SAME WORDS (in the context of "all Excesses are supreme"):

Appendix C

Page 8

FREE-WILL, FREE, FREEDOM, FREE-THINKING, SELF-DETERMINATION, liberty, liberated, voluntary, voluntarily, willfully, without coercion, rights, unrestrained, released, prerogatives, fancy-free, scot-free, rights versus responsibilities, emancipated, emancipation, democratic, democracy, self-rule, self-governing MODERATE, MODERATION, UNEXCESSIVE, NOT EXCESSIVE, ENOUGH, TEMPERATE, THE GOLDEN MEAN, MIDDLE-OF-THE-ROAD, HAPPY MEDIUM, middle-way, temperance, level-headed, adequate, sufficient, discreet, modest COMPROMISE, COMPROMISING, REASONABLE, APPROPRIATE, JUST, JUDICIOUS, IMPARTIAL, TOLERANT, EQUITABLE, OPEN-MINDED, UNBIASED, UNPREJUDICED, OBJECTIVE, FAIR, tolerably, constrained, forbearance, fairly, fair and square, sportsmanlike, nondiscriminatory, prudent, integrate, intermediate, even, equitable, more or less, sort of CHOICES, OPTIONS, CHANGING OPINIONS, EVALUATE, DECIDING, DECISIONS, alternatives, preferences, prerogatives, discretion, select, selections, determine, assess, appraise, pick APPROPRIATE, SUITABLE, VALID, apt, applicable, befitting, fit, fitting, suitable, pertinent, relevant, acceptable, expedient, timely, compatible, desirable, worthy, justified, down-to-earth, matter-of-fact, connected RATIONAL, RATIONALE, RATIONALIZE, REASONING, JUSTIFY, JUSTIFIED, WHY? objective, objectivity, sensible, justification, inquiry, explanation, rationalization, ambiguity DELIBERATE, DEBATE, ARGUE, ARGUMENTS, DISPUTE, DISHARMONY, ANALYZE, controversy, contend, contention, judge, adjudicate, dialectic, rhetoric, conjecture, investigate, analyze, scrutinize, resolve, perceive, perceptive, discern, discerning, cogitate, deduce, derive, surmise, resolve, make up one's mind COMMON SENSE, WISDOM, SENSIBLE, SANE, "NORMAL", making sense, discerning, good judgment, horse sense, insight, sage, sagacity, perspicacity EQUILIBRIUM, COMPOSURE, BALANCED, WELL-BALANCED, strike a balance, "cool", dispassionate WORLDLY DESIRES, NEEDS, WANTS, REQUIREMENTS, WISHES, HOPES, cravings, covet, hunger, longing, yearning, greed, wrong, likes, requests, thirst, pining WORLDLY, MATERIALISM, ungodly, godless, irreligious, mundane, temporal, carnal, corporeal, material, concrete, earthy, earthly, THIS LIFE AND HUMAN BEINGS, PERSONAL INVOLVEMENT, personal entanglement UNBELIEF, DISBELIEF, INQUIRE, SUSPICIOUS, CYNIC, SKEPTIC, SKEPTICISM, UNCERTAIN, UNCERTAINTY, QUESTION, QUESTIONABLE, QUESTIONING, DOUBT, DOUBTERS, INDETERMINATION, DISTRUST, DEBATE, DISPUTE, DISSENT, UNCERTAIN, UNCERTAINTY, UNSURE, INCREDULITY, WHY? intellect, objections, inquisitive, irresolute, unresolved, curiousity, challenge, uncertitude, problematical, agnostic, dubious, disproving, mistrust, arguable, argument, obscure, vague, repudiate, doubting Thomas

(in the context of neutral or "with much thought and purpose" - see N)
UNDISCIPLINED, IRRESPONSIBLE, UNRELIABLE, NOT DEPENDABLE, REBELLING, ANARCHY, STRESS, DISORGANIZED, DISHARMONY, INCONSISTENT, INCONSISTENCY, CHAOS, CONFUSION, disarray, upset, unsettled, insurgent, mutiny, lawlessness, rebellious, unrestrained, irregular, irregularities, commotion, disrupt, disruption, tumult, turmoil, volatile, unfettered, disturbed, disturbance, protest, riot, disintegration, struggle,

Page 9 problems, topsy-turvey, unhinged, mixed-up
(in the context of "with true learning and wisdom" - see N)
> EDUCATION, KNOWLEDGE, learn, learning, training, informed, enlightened, instruction, schooling, teaching, tutor (in the context of "for a great purpose" - see N)
> LIFE, LIFE-ORIENTED, alive, lively, buoyant, effervescent (in the context of "abstract and mental, not tangible or physical" - see N)
> DISCOVERY, EXPLORE, EXPLORATION, reveal, revelation, disclose, expose, aware, ascertain, determine, find out, detect, examine, observe, perceive (in the context of "with much thought and purpose behind it" - see N)
> ADAPTATION, ACCOMODATE, FLEXIBILITY, VERSATILE, COMPROMISE, COORDINATE, CHANGES, CHANGEABLE, CHANGING TIMES, ANYTHING NEW, UNPREDICTABLE, UNKNOWNS, UNCERTAINTY, UNCERTAINTIES, UNSETTLED TIMES, variable, varying, variations, variance, reconcile, reconciliate, resilient, pliable, well-suited, alterations, modifications, mutations, deviation, diversity, differences, unplanned, spontaneous, extemporaneous, unsureness, transformations, conversions, replacements, substitutions, exchanges transform, adjust, shift, fit, tailor-made, acclimate, malleable, many-sided (in the context of "abstract and mental, not tangible or physical" - see C)
> PRACTICAL, PRAGMATIC, functional, workable, useful, utilitarian, constuctive, applicable, feasible, implicit (in the context of "for abstract gain like love, fun, a better future" - see C)
> WORK, JOB, OCCUPATION, CAREER, training, instruction, livelyhood, labor, business, employment, profession, trade, vocation, craft, chores, hard work, strive, toil, effort, make an effort, try, attempt, exertion, perform, handicraft, produce, procedures, process, operate, use, function (in the context of "for abstract gain, like love, fun, a better future" - see C)
> COMPETE, COMPETITION, CONTROVERSY, FIGHT, QUARREL, contend, contention, antagonize, antagonism, conflict, competitor, rival, enemy, contest, aggression, battle, war, warfare, tug-of-war, struggle, animosity, exploit © Copyright 1993
Aaron H. Shovers It is claimed:

1. A programmed computer system for analyzing the personality of a subject, the computer system including an operator input device, and a program including key word lists, each key word list comprising a plurality of words associated with one of six personality types, where the personality types fall into three sets of pairs, a first personality type of each pair precisely opposing a second personality type of the pair, said program being selectively operable to effect the process of:

receiving a text, the text comprising a plurality of words selected by the subject;
  parsing the text for words in each of the six key word lists;
  assigning a weight to any parsed words in the text which are found in at least one of the key word lists;
  associating each parsed word with a respective personality type based upon the word being in a list of that personality type;
  summing for each personality type the weight assigned to each parsed word associated with that personality type; and
  assembling a comparison of the sums for the personality types.

2. A programmed computer system as set forth in claim 1, said program being further selectively operable to effect the process of determining the introversion and extroversion of a subject person.

3. An automated personality analyzer for analyzing the personality of a subject utilizing a plurality of key word lists, each list comprising a plurality of words associated with one of six personality types, where the personality types fall into three sets of pairs, a first personality type of each pair precisely opposing a second personality type of the pair, the analyzer comprising:

a first input device adapted to receive a text, the text comprising a plurality of words selected by the subject; and
  a computer system having:
  means for parsing the text for words in each key word list;
  means for assigning a weight to any parsed words in the text which are found in at least one of the key word lists;
  means for associating each parsed word with a respective personality type based upon the word being in a list of that personality type;
  means for summing for each personality type the weight assigned to each parsed word associated with that personality type;
  means for assembling a comparison of the sums for the six personality types.

4. A method for analyzing the personality of a subject utilizing a plurality of key word lists, each list comprising a plurality of words associated with one of six personality types, where the personality types fall into three sets of pairs, a first personality type of each pair precisely opposing a second personality type of the pair, the method comprising:

receiving a text in a computer system, the text comprising a plurality of words selected by the subject;
  parsing the text in the computer system for words in each key word list;
  assigning a weight in the computer system to any parsed words in the text which are found in at least one of the key word lists;
  associating in the computer system each parsed word with a respective personality type based upon the word being in a list of that personality type;
  summing in the computer system for each personality type the weight assigned to each parsed word associated with that personality type;
  assembling in the computer system a comparison of the sums for the personality types.

5. A method for analyzing the personality of a subject as set forth in claim 4, further comprising the step of, if a parsed word is not found in any of the key word lists, assigning a weight of zero to that word.

6. A method for analyzing the personality of a subject as set forth in claim 4, wherein the assigning step further comprises the steps of, if a parsed word appears in a list, (a) preliminarily assigning a weight to the parsed word;
  (b) if the parsed word was already found in the text, then increasing the weight by a predetermined factor.

7. A method for analyzing the personality of a subject as set forth in claim 4, the key word lists being further subdivided based upon the fit of the word in the list, wherein the assigning step further comprises the steps of, if a parsed word appears in a list, (a) preliminarily assigning a weight to the parsed word;
  (b) increasing the weight by a predetermined factor depending upon the subdivision in which the parsed word is found.

8. A method for analyzing the personality of a subject as set forth in claim 4, the method further comprising:

(a) where data input is from a questionnaire or flashcards, assigning a weight to a subject skipping a question;
  (b) where data input is automated, assigning a weight to long pauses in a monologue;
  (c) where data input is automated, assigning a weight to a volume increases on a key word; and
  (d) factoring the weights obtained in steps a through c into the summed weight for each personality type.

9. A programmed computer system, the computer system comprising a computer program storage medium having a computer program stored thereon for execution by said digital computer, said computer including:

means for receiving a text in the computer, the text comprising a plurality of words selected by the subject;
  means for parsing the text for words in each of a plurality of key word lists, each list comprising a plurality of words associated with one of six personality types, where the personality types fall into three sets of pairs, a first personality _type of each pair precisely opposing a second personality type of the pair;
  means for assigning a weight to any parsed words in the text which are found in each of the key word lists;
  means for associating each parsed word with a respective personality type based upon the word being in a list of that personality type;
  means for summing for each personality type the weight assigned to each parsed word associated with that personality type;
  means for assembling a comparison of the sums for the personality types.

10. A personality analyzer as set forth in claim 9, the program additionally comprising:

(a) means for assigning a weight to a subject skipping a question, where data is input from a questionnaire or flashcards;
  (b) means for assigning a weight to long pauses in a monologue, where data input is automated;
  (c) means for assigning a weight to a volume increases on a key word, where data input is automated; and (d) means for adding the weights of a–c to the weight sum for each personality type.

11. A programmed computer system for classifying words in a text, the computer including an operator input device, and a plurality of key word lists, each comprising a plurality of words associated with one of six personality types, where the personality types fall into three sets of pairs, a first personality type of each pair precisely opposing a second personality type of the pair said program being selectively operable to effect the process of:

parsing a text stored in the computer, the text comprising a plurality of words for words in each key word list;

associating each parsed word with a respective personality type based upon the word being in a list of that personality type.

12. A programmed computer system as set forth in claim 11, wherein a weight is associated with each word in the key word lists, the program further being selectively operable to sum the weights of each associated word, and provide a comparison to the user of the sums.

13. A program as set forth in claim 12 wherein:

(a) for data input from a questionnaire or flashcards, a weight is assigned to a subject skipping a question;

(b) for data input being automated, a weight is assigned to long pauses in a monologue;

(c) for data input being automated, a weight is assigned to a volume increases on a key word; and (d) the weights of steps a through c are summed together with the weight associated with each word in the key word lists to provide a summed weight for each personality type.

14. A programmed computer system as set forth in claim 11, said program being further selectively operable to effect the process of determining the introversion and extroversion of a subject.

15. A programmed computer system for analyzing the personality of a subject, the computer system including an operator input device and a program including six key word lists, each key word list comprising a plurality of words associated with a personality type from the group of Novism, Mutulism, Competism, Revertism, Endurism or Centrism, where Mutulism precisely opposes Competism, Novism precisely opposes Revertism, and Endurism precisely opposes Centrism, said program being selectively operable to effect the process of:

receiving a text, the text comprising a plurality of words selected by the subject;

parsing the text for words in each key word list;

assigning a weight to any parsed words in the text which are found in at least one of the key word lists;

associating each parsed word with a respective personality type based upon the word being in a list of that personality type;

summing for each personality type the weight assigned to each parsed word associated with that personality type; and assembling a comparison of the sums for the personality types.

16. A programmed computer system as set forth in claim 15, said program being further selectively operable to effect the process of determining the introversion and extroversion of a subject person.

17. A programmed computer system as set forth in claim 15 effecting a process comprising the additional steps of:

(a) where data input is from a questionnaire or flashcards, assigning a weight to a subject skipping a question;

(b) where data input is automated, assigning a weight to long pauses in a monologue;

(c) where data input is automated, assigning a weight to a volume increases on a key word; and (d) factoring the weights obtained by steps a through c into the summed weight for each personality type.

18. An automated personality analyzer for analyzing the personality of a subject utilizing six key word lists, each list comprising a plurality of words associated with a personality type from the group of Novism, Mutulism, Competism, Revertism, Endurism and Centrism, where Mutulism precisely opposes Competism, Novism precisely opposes Revertism, and Endurism precisely opposes Centrism, the analyzer comprising:

a first input device adapted to receive a text, the text comprising a plurality of words selected by the subject; and a computer system having:

means for parsing the text for words in each key word list;

means for assigning a weight to any parsed words in the text which are found in at least one of the key word lists;

means for associating each parsed word with a respective personality type based upon the word being in a list of that personality type;

means for summing for each personality type the weight assigned to each parsed word associated with that personality type;

means for assembling a comparison of the sums for the six personality types.

19. An automated personality analyzer as set forth in claim 18, the computer system additionally comprising:

(a) means for assigning a weight to a subject skipping a question, where data is input from a questionnaire or flashcards;

(b) means for assigning a weight to long pauses in a monologue, where data input is automated;

(c) means for assigning a weight to a volume increases on a key word, where data input is automated; and (d) means for adding the weights of a–c to the weight sum for each personality type.

20. A method for analyzing the personality of a subject utilizing six key word lists, each list comprising a plurality of words associated with a personality type from the group of Novism, Mutulism, Competism, Revertism, Endurism and Centrism, where Mutulism precisely opposes Competism, Novism precisely opposes Revertism, and Endurism precisely opposes Centrism, the method comprising:

receiving a text in a computer system, the text comprising a plurality of words selected by the subject;

parsing the text in the computer system for words in each key word list;

assigning a weight in the computer system to any parsed words in the text which are found in at least one of the key word lists;

associating in the computer system each parsed word with a respective personality type based upon the word being in a list of that personality type;

summing in the computer system for each personality type the weight assigned to each parsed word associated with that personality type;

assembling in the computer system a comparison of the sums for the personality types.

21. A method for analyzing the personality of a subject as set forth in claim 20, the method further comprising:
 (a) where data input is from a questionnaire or flashcards, assigning a weight to a subject skipping a question;
 (b) where data input is automated, assigning a weight to long pauses in a monologue;
 (c) where data input is automated, assigning a weight to a volume increases on a key word; and
 (d) factoring the weights obtained in steps a through c into the summed weight for each personality type.

22. A programmed computer system comprising a computer program storage medium having a computer program stored thereon for execution by said digital computer, said computer including:
 means for receiving a text in the computer, the text comprising a plurality of words selected by the subject;
 means for parsing the text for words in each of a plurality of key word lists, each list comprising a plurality of words associated with one of six personality types from the group of Novism, Mutulism, Competism, Revertism, Endurism and Centrism, where Mutulism precisely opposes Competism, Novism precisely opposes Revertism, and Endurism precisely opposes Centrism;
 means for assigning a weight to any parsed words in the text which are found in each of the key word lists;
 means for associating each parsed word with a respective personality type based upon the word being in a list of that personality type;
 means for summing for each personality type the weight assigned to each parsed word associated with that personality type;
 means for assembling a comparison of the sums for the personality types.

23. A programmed computer system as set forth in claim 22, the computer system further including:
 (a) means for assigning a weight to a subject skipping a question, where data is input from a questionnaire or flashcards;
 (b) means for assigning a weight to long pauses in a monologue, where data input is automated;
 (c) means for assigning a weight to a volume increases on a key word, where data input is automated; and
 (d) means for adding the weights of a–c to the weight sum for each personality type.

24. A programmed computer system for classifying words in a text, the computer including an operator input device, and a plurality of key word lists, each list comprising a plurality of words associated with one of six personality types from the group of Novism, Mutulism, Competism, Revertism, Endurism and Centrism, where Mutulism precisely opposes Competism, Novism precisely opposes Revertism, and Endurism precisely opposes Centrism, said program being selectively operable to effect the process of:
 parsing a text stored in the computer, the text comprising a plurality of words for words in each key word list;
 associating each parsed word with a respective personality type based upon the word being in a list of that personality type.

25. A programmed computer system as set forth in claim 24, wherein a weight is associated with each word in the key word lists, the program further being selectively operable to sum the weights of each associated word, and provide a comparison to the user of the sums.

26. A programmed computer system as set forth in claim 24, said program being further selectively operable to effect the process of determining the introversion and extroversion of a subject.

27. A programmed computer system as set forth in claim 24, wherein:
 (a) for data input from a questionnaire or flashcards, a weight is assigned to a subject skipping a question;
 (b) for data input being automated, a weight is assigned to long pauses in a monologue;
 (c) for data input being automated, a weight is assigned to a volume increases on a key word; and
 (d) the weights of steps a through c are summed together with the weight associated with each word in the key word lists to provide a summed weight for each personality type.

* * * * *